(12) United States Patent
Leon et al.

(10) Patent No.: US 11,894,144 B2
(45) Date of Patent: *Feb. 6, 2024

(54) ANIMAL HEALTH DECISION SUPPORT SYSTEM AND METHODS

(71) Applicant: Whiskers Worldwide, LLC, Skokie, IL (US)

(72) Inventors: Debra Leon, Long Grove, IL (US); Trevor Page, Chicago, IL (US); Gunnison Carbone, Orlando, FL (US)

(73) Assignee: Whiskers Worldwide, LLC, Skokie, IL (US)

(*) Notice: Subject to any disclaimer, the term of this patent is extended or adjusted under 35 U.S.C. 154(b) by 523 days.

This patent is subject to a terminal disclaimer.

(21) Appl. No.: 17/089,116

(22) Filed: Nov. 4, 2020

(65) Prior Publication Data

US 2021/0327587 A1 Oct. 21, 2021
US 2022/0148732 A2 May 12, 2022

Related U.S. Application Data

(63) Continuation of application No. 16/811,606, filed on Mar. 6, 2020, which is a continuation-in-part of (Continued)

(51) Int. Cl.
*G16H 50/30* (2018.01)
*G16H 10/60* (2018.01)
(Continued)

(52) U.S. Cl.
CPC .............. *G16H 50/30* (2018.01); *G06N 20/10* (2019.01); *G16H 10/60* (2018.01); *G16H 50/20* (2018.01); *G16H 50/50* (2018.01); *G06N 3/08* (2013.01)

(58) Field of Classification Search
CPC .......... G06N 20/10; G06N 3/08; G16H 10/60; G16H 50/30
See application file for complete search history.

(56) References Cited

U.S. PATENT DOCUMENTS 6,006,191 A 12/1999 DiRienzo
6,208,974 B1 3/2001 Campbell et al.
(Continued)

FOREIGN PATENT DOCUMENTS

CA 2977383 A1 2/2019
CN 108920719 A 11/2018
(Continued)

OTHER PUBLICATIONS

Shuler et al., "Methods, Systems and User Interfaces for Remote Animal Health Monitoring, Assessment, Diagnosis, and Management" Jul. 31, 2013, U.S. Appl. No. 61/860,512, pp. 1-46. (Year: 2013).*

(Continued)

*Primary Examiner* — Miranda M Huang
*Assistant Examiner* — Chase P. Hinckley
(74) *Attorney, Agent, or Firm* — Lathrop GPM LLP; Richard Beem; Alex Shtraym

(57) ABSTRACT

The invention relates generally to a system and method for animal health decision support, and more specifically to a non-human animal health decision support system that is configured to collect animal information, determine a health topic, and transmit a question set corresponding to the health topic. The system may analyze answers associated with the question set to determine a course of action. The course of action may be a recommendation, such as contacting a veterinarian, obtaining a relevant product, making an appointment with a veterinarian, watching for change in symptoms in the non-human animal, and transporting the (Continued)

non-human animal to a clinic. Advantageously, the system is configured to provide decision support and transmit that information to a client device.

20 Claims, 16 Drawing Sheets

Related U.S. Application Data application No. 15/359,033, filed on Nov. 22, 2016, now Pat. No. 10,629,304, which is a continuation-in-part of application No. 14/011,538, filed on Aug. 27, 2013, now abandoned.

(51) Int. Cl.
*G06N 20/10* (2019.01)
*G16H 50/20* (2018.01)
*G16H 50/50* (2018.01)
*G06N 3/08* (2023.01)

(56) References Cited

U.S. PATENT DOCUMENTS

| | | | |
|---|---|---|---|
| 7,076,437 B1 | 7/2006 | Levy | |
| 7,671,751 B2 | 3/2010 | Russell et al. | |
| 8,271,415 B2 | 9/2012 | Iliff | |
| 10,149,617 B2* | 12/2018 | Couse | A61B 5/7275 |
| 10,771,410 B2* | 9/2020 | Lyle | H04L 51/046 |
| 10,930,401 B2* | 2/2021 | Olives | G16H 50/30 |
| 11,361,368 B2* | 6/2022 | Bramson | G16H 30/40 |
| 11,564,572 B2* | 1/2023 | Maher | A61B 5/6831 |
| 2001/0051765 A1 | 12/2001 | Walker et al. | |
| 2003/0004655 A1 | 1/2003 | Singh et al. | |
| 2003/0012705 A1 | 1/2003 | Singh | |
| 2003/0166996 A1 | 9/2003 | Kim et al. | |
| 2003/0212574 A1 | 11/2003 | Olivier | |
| 2003/0229452 A1 | 12/2003 | Lewis et al. | |
| 2004/0230607 A1 | 11/2004 | Pawlick | |
| 2005/0032034 A1 | 2/2005 | Dodds | |
| 2005/0108052 A1 | 5/2005 | Omaboe | |
| 2006/0038010 A1 | 2/2006 | Lucas | |
| 2006/0064250 A1 | 3/2006 | Goldstein | |
| 2007/0143151 A1 | 6/2007 | Fey et al. | |
| 2007/0174253 A1 | 7/2007 | Hodnett et al. | |
| 2007/0226257 A1 | 9/2007 | Yarnall, Jr. | |
| 2008/0058670 A1 | 3/2008 | Mainini | |
| 2008/0097809 A1 | 4/2008 | Stroman et al. | |
| 2008/0162175 A1 | 7/2008 | Paige et al. | |
| 2008/0312511 A1 | 12/2008 | Osler et al. | |
| 2009/0006419 A1 | 1/2009 | Savitsky et al. | |
| 2009/0062623 A1 | 3/2009 | Cohen et al. | |
| 2009/0106044 A1 | 4/2009 | Schweisguth et al. | |
| 2009/0138310 A1* | 5/2009 | Beall | G06Q 30/0601 |
| | | | 705/26.1 |
| 2009/0175980 A1 | 7/2009 | Willcocks et al. | |
| 2009/0187392 A1* | 7/2009 | Riskey | A61B 5/4238 |
| | | | 703/11 |
| 2009/0234916 A1 | 9/2009 | Cosentino et al. | |
| 2010/0121156 A1 | 5/2010 | Yoo | |
| 2010/0261981 A1 | 10/2010 | Griffioen | |
| 2011/0010380 A1 | 1/2011 | Chen | |
| 2011/0054978 A1 | 3/2011 | Mohil | |
| 2011/0093295 A1 | 4/2011 | Mankad et al. | |
| 2011/0213625 A1 | 9/2011 | Joao | |
| 2011/0302117 A1 | 12/2011 | Pinckney et al. | |
| 2012/0124387 A1* | 5/2012 | Skocic | A01K 11/006 |
| | | | 713/186 |
| 2013/0046552 A1 | 2/2013 | Verstandig et al. | |
| 2013/0095459 A1 | 4/2013 | Tran | |
| 2013/0096942 A1 | 4/2013 | Bowles et al. | |
| 2013/0173439 A1 | 7/2013 | Christiansen | |
| 2013/0185097 A1 | 7/2013 | Saria et al. | |
| 2013/0198175 A1* | 8/2013 | Thalheim | G06F 16/2471 |
| | | | 707/723 |
| 2013/0297553 A1* | 11/2013 | Bierner | G06N 5/02 |
| | | | 706/46 |
| 2014/0019162 A1 | 1/2014 | Skowronski et al. | |
| 2014/0046698 A1 | 2/2014 | Skocic | |
| 2014/0052463 A1* | 2/2014 | Cashman | G06Q 10/1095 |
| | | | 705/2 |
| 2014/0182519 A1 | 7/2014 | Tupin, Jr. | |
| 2014/0228648 A1 | 8/2014 | Goldberg et al. | |
| 2014/0275824 A1 | 9/2014 | Couse | |
| 2014/0304200 A1 | 10/2014 | Wall | |
| 2014/0316805 A1 | 10/2014 | Nagata | |
| 2015/0039239 A1* | 2/2015 | Shuler | G16H 40/67 |
| | | | 702/19 |
| 2015/0057963 A1 | 2/2015 | Zakharov et al. | |
| 2015/0066520 A1 | 3/2015 | Leon et al. | |
| 2016/0012748 A1* | 1/2016 | Donavon | G09B 19/0092 |
| | | | 434/225 |
| 2016/0026765 A1* | 1/2016 | Daines | G16H 50/20 |
| | | | 705/3 |
| 2016/0063188 A1 | 3/2016 | Thornberry et al. | |
| 2016/0192620 A1 | 7/2016 | Hu et al. | |
| 2016/0246934 A1* | 8/2016 | Dunlop | G16H 70/20 |
| 2017/0032241 A1* | 2/2017 | Corrado | G16H 50/30 |
| 2018/0144099 A1 | 5/2018 | Leon et al. | |
| 2020/0239966 A1* | 7/2020 | Breen | G01N 33/5743 |
| 2020/0381119 A1* | 12/2020 | Gibbs | G16H 40/67 |
| 2021/0186059 A1* | 6/2021 | Brockman | A23K 50/40 |
| 2021/0319895 A1 | 10/2021 | Joao | |
| 2021/0327589 A1 | 10/2021 | Bradley et al. | |
| 2022/0005607 A1 | 1/2022 | Holcombe et al. | |
| 2022/0039358 A1 | 2/2022 | Wernimont et al. | |
| 2022/0044788 A1 | 2/2022 | Wernimont et al. | |
| 2022/0044815 A1 | 2/2022 | Shaw et al. | |
| 2022/0139553 A1* | 5/2022 | Majamaa | G16H 10/60 |
| | | | 705/2 |
| 2022/0334705 A1* | 10/2022 | Tai | G06F 3/04845 |

FOREIGN PATENT DOCUMENTS

| | | |
|---|---|---|
| CN | 108935317 A | 12/2018 |
| CN | 109036542 A | 12/2018 |
| CN | 109064011 A | 12/2018 |
| CN | 109064012 A | 12/2018 |
| CN | 208211175 U | 12/2018 |
| EP | 2472487 A2 | 7/2012 |
| EP | 3264299 A1 | 3/2018 |
| EP | 1892657 | 6/2019 |
| GB | 2347503 A | 9/2000 |
| JP | 2003-141240 | 5/2003 |
| JP | 4688512 | 6/2019 |
| JP | 2002197290 | 10/2019 |
| JP | 4832948 | 12/2019 |
| KR | 20180106592 A | 10/2018 |
| KR | 20030070866 | 6/2019 |
| KR | 20060058446 | 6/2019 |
| WO | 2005029387 | 3/2005 |
| WO | 2005029387 A1 | 3/2005 |
| WO | 2018118714 A1 | 6/2018 |
| WO | 2019143714 A1 | 7/2019 |

OTHER PUBLICATIONS

Madder et al., "e-Surveillance in Animal Health: use and evaluation of mobile tools" Apr. 13, 2012, pp. 1831-1842. (Year: 2012).*
Garg et Mony, "Electronic data capture for health surveys in developing countries: use of a mobile phone based application in southern India" Jun. 30, 2013, pp. 1-10. (Year: 2013).*
Carse, Stephen James, "A Veterinary Diagnosis Expert System for Remote Use" 2013, pp. 1-95. (Year: 2013).*
PetMD, available as of Jul. 18, 2013 at http://www.petmd.com/.
Web DVM, available as of Jul. 18, 2013 at http://web-dvm.net/.
ZOOTOO, available as of Jul. 18, 2013 at http://www.zootoo.com/.
HelpMyHound, available as of Jul. 18, 2013 at http://helpmyhound.com/.
HomeAgain, available as of Jul. 18, 2013 at http://public.homeagain.com/pet-emergency.html.

(56) References Cited

OTHER PUBLICATIONS

Veterinary Partner, available as of Jul. 18, 2013 at http://www.veterinarypartner.com/.
Justanswer. Pet, available as of Jul. 18, 2013 at http://www.justanswer.com/pet/.
Pet WebMD, available as of Jul. 18, 2013 at http://pets.webmd.com/.
Veterinarian Advice Online, available as of Jul. 18, 2013 at http://www.free-online-veterinarian-advice.com/.
AskVetAdvice.com, available as of Jul. 18, 2013 at http://www.askvetadvice.com/.
AskAVetQuestion.com, available as of Jul. 18, 2013 at http://www.askavetquestion.com/.
www.webMD.com/phr—Apr. 21, 2012—https://web.archive.org/web/20120421063410/http://www.webmd.com/phr.
PetMD.com—Jun. 1, 2012—(https://web.archive.org/web/20120601174536/http://www.petmd.com/).
PetMD.com App Article—Oct. 18, 2012—(http://www.petmd.com/news/care-safety/nws_multi_cat_dog_symptom_checker_app_launch-29241).
Thakre et al. Zigbee Based Health Monitoring and Feedback System in Animal Health Care. International Journal of Innovative Research in Science, Engineering and Technology, vol. 6, Special Issue 11, May 2017. (5 pages).
Kumar et al. Dog Health Management Trainer: An Effective eLearning System for Dog Owners and Practitioners. Journal of the Indian Society of Agricultural Statistics, 70(1) 2016, pp. 83-89. (8 pages).
Johnson et al. An Innovative New Approach to Animal Care. IEEE. 2018. (2 pages).
Bhavsar et al. ZigBee Based Network Architecture for Animal Health Monitoring. IEEE. Sep. 4-5, 2015. (2 pages).
Cheng et al. caRemote: The Design of a Cancer Reporting and Monitoring Telemedicine System for Domestic Care. IEEE. Aug. 30-Sep. 3, 2011. (4 pages).
Karimuribo et al. Towards One Health disease surveillance: The Southern African Centre for Infectious Disease Surveillance approach. Onderstepoort Journal of Veterinary Research. 2012. (7 pages).
Kristensen et al. A mixed methods inquiry: How dairy farmers perceive the value(s) of their involvement in an intensive dairy herd health management program. Acta Veterinaria Scandinavica. Dec. 18, 2008. (12 pages).
Langstaff. Smart surveillance with smartphones. Australian Veterinary Journal. Dec. 2012. (2 pages).
Li et al. Decision Support System for the Response to Infectious Disease Emergencies Based on WebGIS and Mobile Services in China. PLOS One. (12 pages).
Lin et al. Addressing Animal Health Knowledge Gaps in Southern Countries: The Creation of a 2D Animal Health Resource Room. The Livestock Development Group, School of Agriculture, Policy and Development, University of Reading. 2009. (27 pages).
Madder et al. e-Surveillance in Animal Health: use and evaluation of mobile tools. Parasitology. Apr. 13, 2012. (12 pages).
Robertson et al. Mobile Phone-based Infectious Disease Surveillance System, Sri Lanka. Emerging Infectious Diseases. Oct. 10, 2010. (8 pages).
Sawford et al. A Focused Ethnographic Study of Sri Lankan Government Field Veterinarians' Decision Making about Diagnostic Laboratory Submissions and Perceptions of Surveillance. PLOS One. Oct. 25, 2012. (11 pages).
Sawford, Kate Elizabeth. Animal health surveillance for early detection of emerging infectious disease risks. PhD Thesis, University of Calgary. Dec. 2011. (247 pages).
Smedberg, Asa. Enabling Cross-Usage of Public Health Surveillance—A Holistic Approach to Ask the Expert Systems and Online Communities. The Department of Computer and Systems Sciences, Stockholm University/The Royal Institute of Technology, Kista, Sweden. 2008. (5 pages).
Weaver, Alice Malia. Fort Collins Veterinary Practices and Websites: How Telemedicine is Used as a Marketing Tool. Masters Thesis, Colorado State University. 2012. (174 pages).
U.S. Appl. No. 16/811,606, Non-Final Office Action dated Mar. 15, 2023, 26 pages.
Zhang et al., Large-Scale Generative Modeling to Improve Automated Veterinary Disese Coding, (arXiv:1811.11958v1).
Ristokski et al., RDF2Vec: RDF Graph Embeddings and Their Applications.
Zhang et al., VetTag: Improving Automated Veterinary Disgnosis Coding via Large-Scale Language Modeling.
Kalaivani et al., An Ontology Construction Approach for the Domain of Poultry Science Using Protege.
Zini et al., Predictors of Clinical Remission in Cats with Diabetes Mellitus.

* cited by examiner

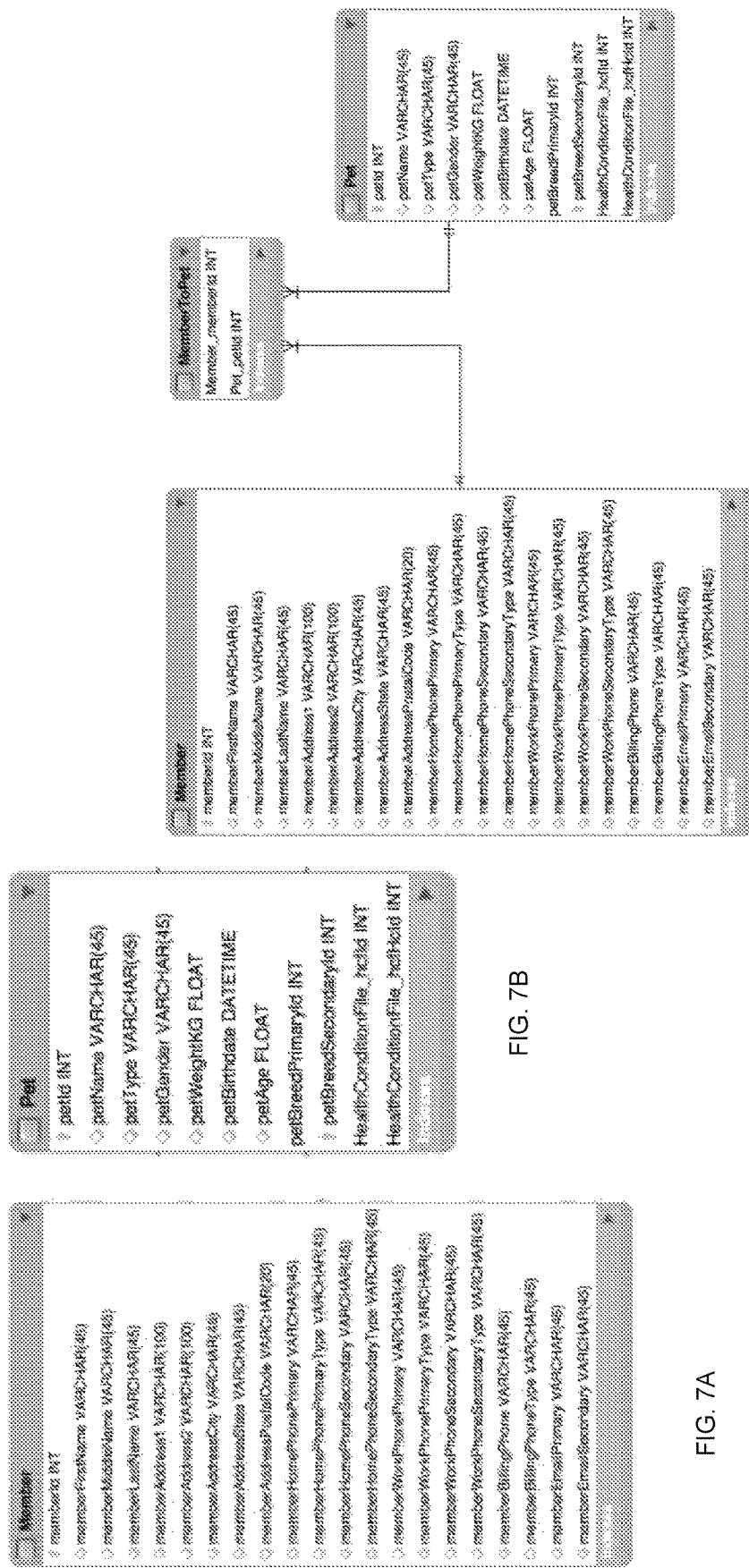

ANIMAL HEALTH DECISION SUPPORT SYSTEM AND METHODS

PRIORITY

This application is a continuation of U.S. application Ser. No. 16/811,606 filed Mar. 6, 2020, which is a continuation-in-part of U.S. application Ser. No. 15/359,033 filed Nov. 22, 2016 (now U.S. Pat. No. 10,629,304), which is a continuation-in-part of U.S. application Ser. No. 14/011,538 filed Aug. 27, 2013, each of which is hereby incorporated by reference in its entirety.

BACKGROUND OF INVENTION

The claims in the instant application are different than those of the parent application or other related applications. The Applicant therefore rescinds any disclaimer of claim scope made in the parent application or any predecessor application in relation to the instant application. Any such previous disclaimer and any cited references may need to be revisited. Further, any disclaimer made in the instant application should not be read into or against the parent application.

TECHNICAL FIELD

The invention relates generally to a system and method for integrating pet health records, and more specifically to an integrated pet health record that is configured to collect, store, maintain, analyze, and provide recommendations about a pet's health from a variety of sources.

RELATED ART

Traditionally, when a pet is acting differently than normal or even exhibiting concerning symptoms, the pet owner's only option is to take the pet to a doctor of veterinary medicine ("veterinarian," "DVM", "VMD" or "vet"). If the situation occurs after hours, the options are more limited and costly. In addition, access to a Veterinary Emergency Clinic is often limited by geography (clinics can be hundreds of miles away). While taking the pet to a veterinarian is often the right course of action, in many situations it is not necessary to take a pet to a veterinarian immediately, if at all.

At the same time, the pet owner likely does not have sufficient knowledge to fully appreciate the mildness or severity of the pet's condition, so the owner may not know whether the pet's malady is serious enough as to require immediate attention or whether it is something that may be monitored and managed without professional intervention. In these situations, the owner may elect to err on the side of caution and bring the pet to the vet, even when it turns out that a more passive approach may be sufficient. While the owner has the pet's best interests in mind, these frequent visits to a DVM in non-emergency situations may become expensive and inconvenient for the pet owner. This is also an inefficient use of DVM resources and may delay care for animals in immediate need of DVM care. In addition, a common issue for dogs and cats is anxiety, which is exacerbated by a visit to a vet; as a result, unnecessary veterinary visits can have adverse health impact on the pet. Cats in particular are prone to severe anxiety when transported in a car and taken away from their familiar environment.

In some existing systems, stand-alone applications are used to provide pet medical advice to users. Typically, the questions and answers in these stand-alone applications are integrated into the executable file for the application or other locally stored application files. This approach has several drawbacks. For example, whenever the content of the tutorial needs to be changed or updated, the entire application needs to be recompiled and redistributed to each user. This is difficult on the application developer as they must have knowledge of the code to know what to change and must take care to avoid causing errors in other aspects of the code. Additionally, this may require approval from a third party for the new application, such as on mobile phone app stores, to release the latest tutorial, which can lead to delays. This also requires users to maintain the most current, up-to-date version of the application installed to access the latest version of a tutorial. If a user does not update the application, she may be accessing an out-of-date or incorrect tutorial.

Others have used web-based tutorials to provide medical advice to users. This approach also suffers drawbacks however, such as requiring a constant internet connection. If at any point in the tutorial, a user loses an internet connection, their place in the tutorial is lost and they will be required to restart the tutorial, requiring more time and computer resources. Moreover, none of the above-mentioned systems incorporate the specifics of each individual pet into the algorithm so that the answers are general and may not accurately reflect the necessary information for a specific pet.

Additionally, pet medical records are typically generated for pets in veterinary offices. However, those are brief snapshots of a pet's health. They don't capture the full day-to-day issues that a pet may have. Smaller perceived problems, those in which the pet parent doesn't take their pet to the veterinarian, are not part of the pet's medical record. Those smaller problems can, over time, become larger issues—often to the lower quality of life for the pet.

Accordingly, a need has long existed for an improved pet health record system and methods for animal health care decision support.

SUMMARY

The invention relates generally to a system and method for integrating pet health records, and more specifically to an integrated pet health record that is configured to collect, store, maintain, analyze, and provide recommendations about a pet's health from a variety of sources. The integrated pet health record system solves various technical problems associated with prior systems for collecting, storing, and maintaining a health record.

The integration of the pet health record may occur over a network, such as the Internet. A server-side application or middleware component may expose a RESTful API to clients. These clients are the integration points, composed of software processes that deliver data to the server-side application. Data is in the form of both text-based information and binary information such as photos and videos. Examples of software clients that may deliver data to the server-side application include brick-and-mortar veterinary medical record software, telehealth/telemedicine software, Q&A self-service interactive software, data gathered while browsing topics on website/in-app, other pet health content-based software, and wearable devices, such as a collar.

The system may analyze health conditions for an animal on both an individual basis and in regards to a global population. This analysis provides an assessment of the pet based on a number of factors including pet type, breed, age, weight, geographic location, living conditions, diet, and exercise. All of these factors influence recognition of health conditions based on causes and symptoms, and how treatments can be refined to improve outcomes.

Certain embodiments of the system may include a thin client application that downloads question sets from a server. The question sets may include a series of interlinked questions and answers as well as scores associated with the answers. Scores of selected answers may be tallied and a decision corresponding to the cumulative score of the selected answers may be provided to a user. As a result, the system may enable the ability to update (add, revise or delete) questions, answers and question lines without needing to recompile and redistribute the client application. In addition, the transmission of a complete question set reduces overall network traffic and technical problems arising from network disruptions among other technical benefits.

In certain embodiments, a system for providing animal related health care decision support is provided. The system may include a software module for use on a mobile device, the software module including instructions stored on a non-transitory computer readable medium that: present an animal related health topic to a user; receive a selection of the animal related health topic from the user; request, from a server computer, a question set related to the selected animal related health topic, the question set including one or more questions, each question having one or more associated answers; receive, from the server computer, the question set; display one or more questions from the question set; receive selections of answers associated with the displayed questions; determine a course of action based on the selected answers; and display the determined course of action.

In certain embodiments, a method for providing decision support may be provided. The method may include: presenting an animal related health topic to a user; receiving a selection of the animal related health topic from the user; requesting, from a server computer, a question set related to the selected animal related health topic, the question set including one or more questions, each question having one or more associated answers; receiving, from the server computer, the question set; displaying one or more questions from the question set; receiving selections of answers associated with the displayed questions; determining a course of action based on the selected answers; and displaying the determined course of action.

In certain embodiments, a system for providing animal related health care decision support may be provided. The system may include a first software module for use on a mobile device, the software module including instructions stored on a non-transitory computer readable medium that: present an animal related health topic to a user; receive a selection of the animal related health topic from the user; request, from a server computer, a question set related to the selected animal related health topic, the question set including one or more questions, each question having one or more associated answers; receive, from the server computer, the question set; display one or more questions from the question set; receive selections of answers associated with the displayed questions; determine a course of action based on the selected answers; and display the determined course of action. The system also may include a second software module for use on a server computer, the second software module including instructions stored on a non-transitory computer readable medium that: receive the request for the question set related to the selected animal related health topic; and transmit a question set related to the selected animal related health topic, the question set including one or more questions, each question having one or more associated answers.

Other systems, methods, features, and technical advantages of the invention will be, or will become apparent to one with skill in the art upon examination of the following figures and detailed description. It is intended that all such additional systems, methods, features, and technical advantages be included within this description, be within the scope of the invention, and be protected by the following claims.

BRIEF DESCRIPTION OF THE DRAWINGS

The invention may be better understood with reference to the following drawings and description. The components in the figures are not necessarily to scale, emphasis instead being placed upon illustrating the principles of the invention.

FIG. 7A illustrates and exemplary relationship of data formed by the database schema of the system;

FIG. 7B illustrates and exemplary relationship of data formed by the database schema of the system;

FIG. 7C illustrates and exemplary relationship of data formed by the database schema of the system;

DETAILED DESCRIPTION OF THE PREFERRED EMBODIMENTS

The elements illustrated in the figures interoperate as explained in more detail below. Before setting forth the detailed explanation, however, it is noted that all of the discussion below, regardless of the particular implementation being described, is exemplary in nature, rather than limiting. For example, although selected aspects, features, or components of the implementations are depicted as being stored in memories, all or part of systems and methods consistent with the contact management system architecture may be stored on, distributed across, or read from other machine-readable media, for example, secondary storage devices such as hard disks, floppy disks, and CD-ROMs; a signal received from a network; other forms of ROM or RAM either currently known or later developed; and the like.

Furthermore, although specific components of the communications architecture will be described, methods, systems, and articles of manufacture consistent with the decision support system architecture may include additional or different components. For example, a processor may be implemented as a microprocessor, microcontroller, application specific integrated circuit (ASIC), discrete logic, or a combination of other type of circuits or logic. Similarly, memories may be DRAM, SRAM, Flash or any other type of memory. Flags, data, databases, tables, and other data structures may be separately stored and managed, may be incorporated into a single memory or database, may be distributed, or may be logically and physically organized in many different ways, including unstructured data. Programs may be parts of a single program, separate programs, or distributed across several memories and processors. Systems may be implemented in hardware, software, or a combination of hardware and software in one processing system or distributed across multiple processing systems.

While the system may be used to generate a health record in various areas, it may be particularly well suited to the realm of an integrated pet health record. In that regard, the system may receive a plurality of user inputs relating to user observations or subjective assessments with the goal of recommending a next course of action from among a plurality of possible options.

1.0 Exemplary System Overview

Figure 1:
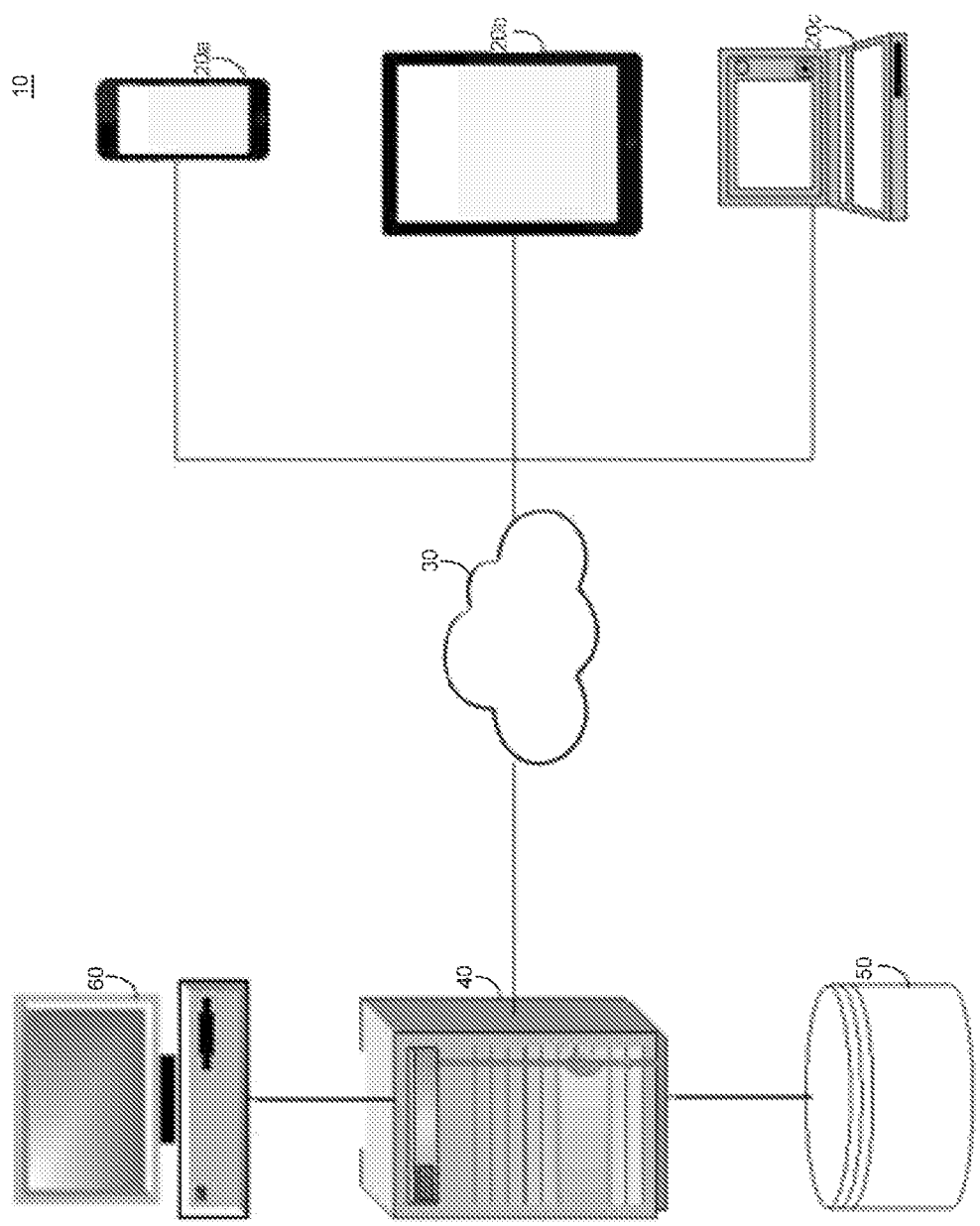
FIG. 1 shows an exemplary physical architecture for an exemplary system for answering a pet health query.

Referring to FIG. 1, an exemplary physical architecture 10 for an integrated pet health record system 10 for maintaining, analyzing, and providing recommendations about a pet's health from a variety of sources. One or more client devices 20a-c may run client application 100 (see FIG. 2) that may communicate with a server 40 via a communications network 30 (shown as an exemplary Internet cloud). The client applications may request pet health topics, questions, and/or answers from the server 40 and present the same to a user. The client applications also may receive input from the user, such as user selections of answers to questions, user profile information and the like, and determine an appropriate course of action based on the user's selections and present that course of action to a user, among other functions described herein. The server 40 may provide the topics, questions, and/or answers to client applications based on received requests, such as queries and the like. The server 40 also may store information in a database 50 and also may provide an administration interface 60 that enables an administrator to interact with the server 40.

Although references will now be made to specific components of the system performing specific features, it should be apparent to one of ordinary skill in the art that such references are exemplary and are not intended to limit the scope of the claims in any way; furthermore, the functionalities described herein may be implemented in a virtually unlimited number of configurations. For example, although figuratively attached to the server 40, the database 50 may, in practice, distribute user-specific data elements directly to one or more client devices 20a, 20b, and 20c. Similarly, the server 40 may be implemented as a single server configured to provide all of the system's functionalities, or the functionalities may be implemented across multiple servers.

1.1 Exemplary Client Applications

The client applications may provide a user interface for the system 10 and may communicate user profile and other information with the server 40 via communications network 30. In one embodiment, client applications may comprise stand-alone applications which may be either platform dependent or platform independent. For example, client applications may be stand-alone applications for a mobile phone configured to run on a mobile operating system such as the iOS™ operating system from Apple Inc. located in Cupertino, California, the Android™ operating system from Google, Inc. located in Mountain View, California, or the like. Alternatively, or additionally, client devices 20a-c may connect to the server 40 via the Internet using a standard browser application. Alternatively, or additionally, one or more of the client applications may be an application configured to run on mobile computer such as a laptop computer, handheld computer, wearable device, tablet, mobile messaging device, or the like which may all utilize different hardware and/or software packages. Other methods may be used to implement the client applications.

In operation, client devices 20a-c may operate in conjunction with server 40, for example, to allow a user to register with the server 40, enter health information about the pet, conduct pet health topic searches, answer pet health related questions, receive recommendations for veterinary care and the like. Client application 20a-c also may provide other functions, such as present options for users to look up pet help by category, present information about relevant products and knowledge bases, contact a veterinarian by email, chat or voice communication channels, find a local veterinarian, and the like. As should be apparent to one of ordinary skill in the art from the disclosure herein, other related services may also be provided.

A user may be an individual, a commercial entity, or any other type of entity. For example, an individual user may be a person who owns a pet. Alternatively, or additionally, an individual user may be a person in temporary care of a pet. An exemplary commercial entity user may be a professional health care provider or a representative thereof, such as a veterinarian, veterinarian nurse, technician, or the like.

1.2 Exemplary Communications Networks 30

The communications network 30 may be any private or public communication network, such as the Internet, and may include one or more communications networks. In some embodiments, the communications network 30 may be the Internet or the like.

1.3 Exemplary Pet Record Server 40

The server 40 may include a server-side application 106 configured to expose, for example, a Representational State Transfer (REST) API to client devices 20a-c. These clients are the integration points, composed of software processes that deliver data to the server-side application 106.

The server-side application 106 is configured to integrate, consume, and analyze data. For purposes of this application, consuming data refers to the processing and storage of data into organized formats for database storage. Consuming the data requires the server-side application 106 to maintain the data in both a logical and flexible format such that new data can be easily added to the record. For example, the data may be primarily stored and optimized in a relational database.

The capture of data occurs before it is consumed by the server-side application 106. Data capture includes integration with a legacy or existing medical record system and conversion of data to a format readable by the system. Translation or conversion software may convert data from an existing format into one used by the current system. For example, the system may create rules to translate data from an existing format into one expected by the system 10. Data in existing formats is typically in a relational database format and conversion may involve mapping of tables and fields in that format to a version the system 10 understands.

In certain preferred embodiments, the data is converted into a Resource Description Framework (RDF) format. The system may construct data in RDF format to generate a labeled and directed graph. The RDF graph may be constructed of nodes and edges. Data relating to an animal or a health condition of the animal have properties such as the name of the animal or medical condition. The system may then use a Universal Resource Identifier (URI)—a global identifier—to identify that data.

The server 40 may capture data through self-service software applications or on an assisted basis with a healthcare provider. Self-service data capture may involve receiving the inputs from a software application based on user inputs. Such applications may provide a user interface that makes it simple for non-healthcare personnel to generate structured medical information.

For data capture on an assisted basis, a veterinarian, veterinarian nurse or technician, or similar healthcare provider may transmit data to the system at the point of care. The healthcare provider may be in direct contact with the patient and pet parent, or via a long-distance relationship such as a phone call, Internet-based video call, or text-based chat.

The server may store captured data for the pet and pet parent, such as user profiles, pet health questions, pet health answers, and other information, in a database 50, receive search requests from a client application 20a-c, communicate with various third parties (such as veterinarians and the like), provide a user interface for an administration application 60, and the like. In operation, the server 40 and client devices 20a-c may, for example, be configured to register a user with the server 40, conduct pet health topic searches, provide recommendations for veterinary care, provide hyperlinks to relevant products and knowledge bases, and the like. Additional examples of pet parent data captured by the system include name, address, and contact information. Examples of pet data captured by the system include pet name, type of pet, breed, gender, age, weight, and spayed/neutered status. The system is configured to detect changes in the pet data—such as the pet weight—and determine symptoms, tests, causes, treatments, and outcomes. As should be apparent to one of ordinary skill in the art from the disclosure herein, other related services may also be provided.

The database 50 may store a variety of information, including user profile information, user preference information, pet health question sets, pet health answers, decision trees, veterinary contact information, product hyperlinks, and the like. In certain embodiments, all information stored in the database 50 is encrypted.

The system may facilitate communication with other health record systems through use of a Representational State Transfer (REST) software data structure. REST allows for the creation of web services, which may operate via the Internet over standard protocols such as HTTP.

The RESTful API may utilizes data in JavaScript Object Notation (JSON) format for communication between software applications that are collecting the data (clients) and a relational database that maintains the integrated data. JSON provides a human-readable and flexible format whereby fields and associated data are combined into a document format.

The following is exemplary code for storing pet information in a JSON format:
"pets": [
{
"petName": "Fred",
"petId": 1,
"memberId": "12345",
"petType": "Dog",
"petGender": "Male",
"petBreed": "Cockapoo",
"petAge": "3",
"petFixed": "No",
"petNumber": "123456"
}]

The delivery of JSON-encoded data from a client device 20a-c to the service 40 is through a series of API services that include create, read, update, and delete (CRUD) operations for pet parent data, pet data, and other data related to medical interactions and health issues.

Once data is captured by the system through the RESTful API, it is then translated from a JSON format into a relational database. In certain embodiments, the system 10 utilizes an origination field as part of the conversion process from a legacy or existing data store. The origination field facilitates tracking the data in the system 10 back to its original source. A relational database of the system may then define relationships between data entities stored in tables, for example, according to a database schema. Data may be mapped from the JSON format into relational tables, with checks for old, redundant, or duplicate data.

In some embodiments, the server 40 and database 50 may comprise one or more instances of a GoDaddy™ Virtual Private Server (provided by GoDaddy Operating Company, LLC of Scottsdale, Ariz.) running the Windows Server 2012™ operating system (provided by Microsoft Corporation of Redmond, Wash.) utilizing one or more of relational databases and/or other storage mechanisms.

1.4 Exemplary Administrative Application 60

Figure 6:
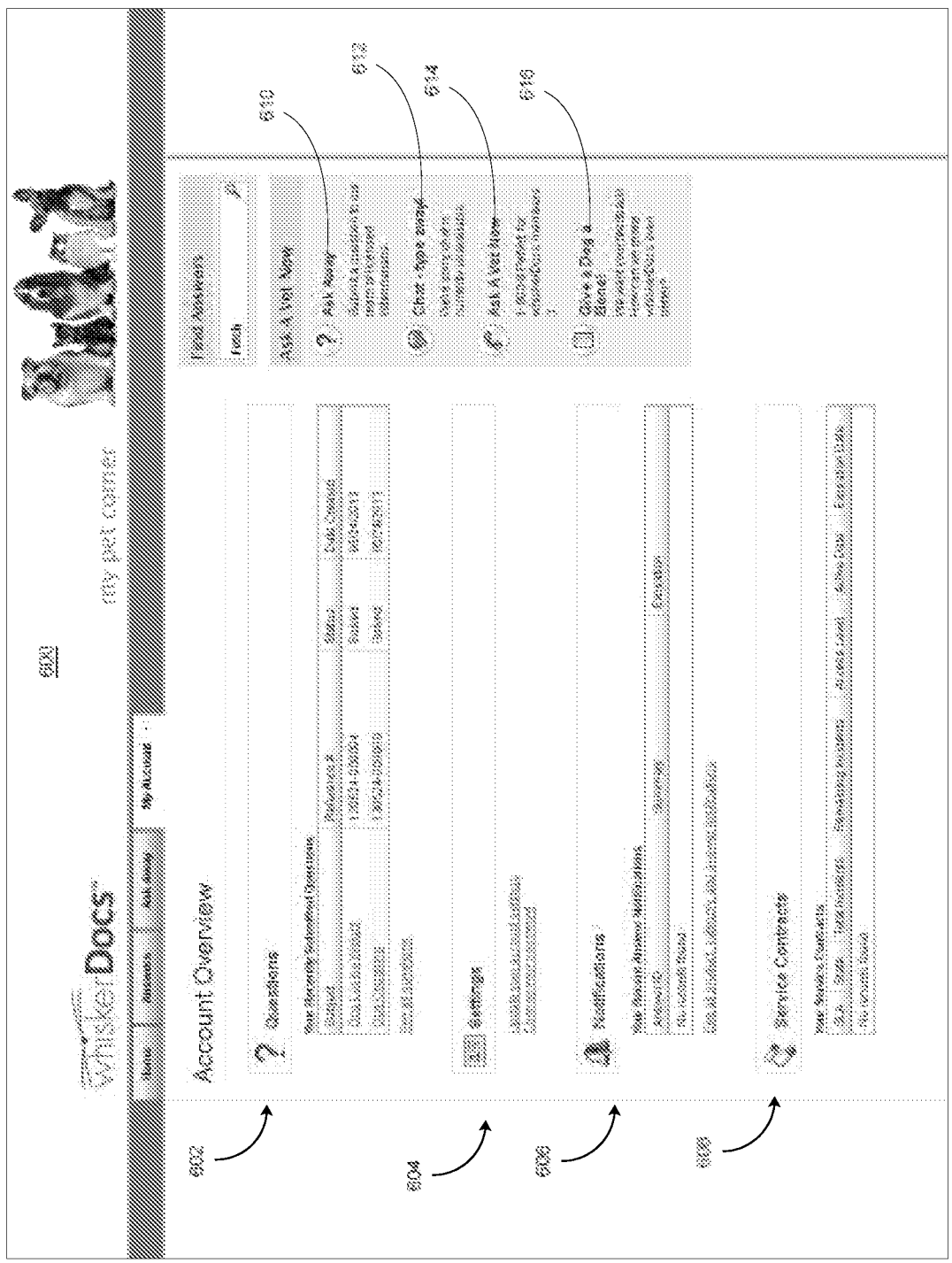
FIG. 6 shows an exemplary screenshot of a user account page on a web portal.

In some embodiments, the system 10 may include an administration application 600. The administration application 600 may be provided by the server 40, for example, as a stand-alone application running on a computer such as a workstation computer, laptop computer, handheld computer, tablet, mobile messaging device, or the like which may all utilize different hardware and/or software packages. Alternatively, or additionally, administration application 60 may connect to the server 40 via the Internet using a standard browser application. A browser based implementation allows system features to be accessible regardless of the underlying platform of the administration application 600. Other methods may be used to implement the administration application 600. As should be apparent to one of ordinary skill in the art from the disclosure herein, other related services may also be provided. An exemplary screenshot of a user interface for an administration application 600 is shown in FIG. 6.

2.0 Exemplary Process

Figure 2:
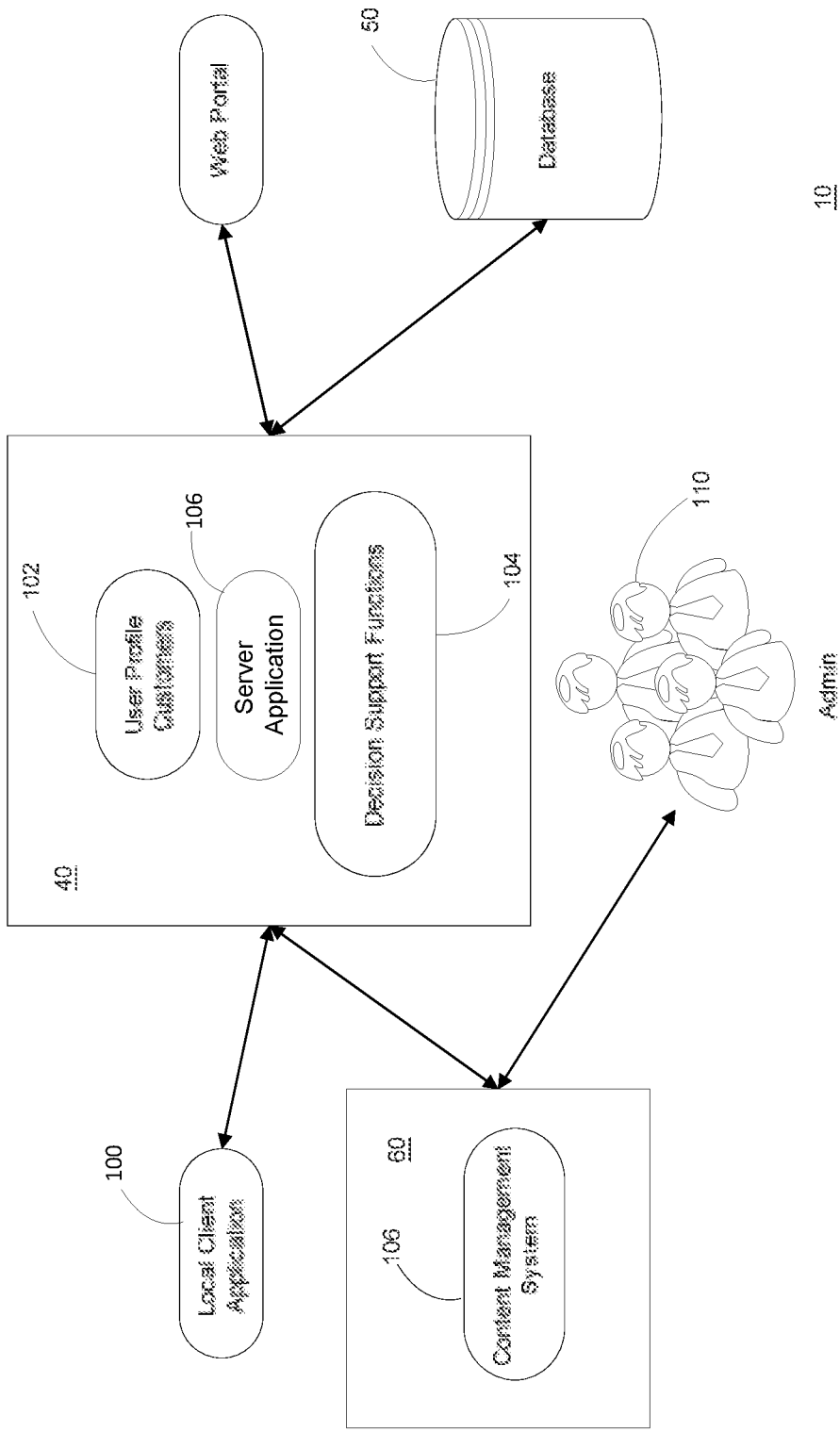
FIG. 2 shows an exemplary functional architecture for an exemplary system for answering a pet health query.

FIG. 2 shows an exemplary functional architecture of one embodiment of integrated health care record system 10. Server 40 may provide a way for local client application 100 to access user account functionality 102 and decision support functionality 104 as well as database 50. In addition, content management functionality 106 may be accessible via the administration application 600 as described above.

2.1 Exemplary User Account Functions

In some embodiments, users may access a user account functions 102 to create an account. A user also may access a portal on a local client application on one of the devices listed above. A user may access a customer portal on a client application of a local computing device, for example, by requesting the customer portal from a web server. Several components of the system may apply whether the user is logged in to his or her account or not, although additional components may be available to logged in users. For example, both logged out and logged in users may be able to progress through question sets, as discussed below, but responses entered by a logged in user also may be added to a record generated for the user or pet, which may be formatted and/or transmitted to the user's veterinary provider.

On subsequent "Create a Profile" pages, the system may present further queries and fillable fields to the user regarding additional pet demographic and health information, including but not limited to age, gender, species, breed, and pre-existing conditions, for each pet entered by the user. The system also may include an option to upload other documents related to a health record of a pet, including past records from a veterinarian. Any uploaded files may be stored in a database of the system, such as database 50, and may be accessible to the user upon logging in and accessing the account tab on the customer portal homepage.

The user account or profile may be stored in the database associated with the cloud customer relationship management (CRM) platform, and the user may be returned to the customer portal homepage, thereby completing the registration process. Again, this information may be submitted at a different time, such as during part of the decision support process, although it may be beneficial to provide it at an outset so that it may be available readily across multiple query sessions at different times.

2.2 Exemplary Self-Service Functions

Figure 3:
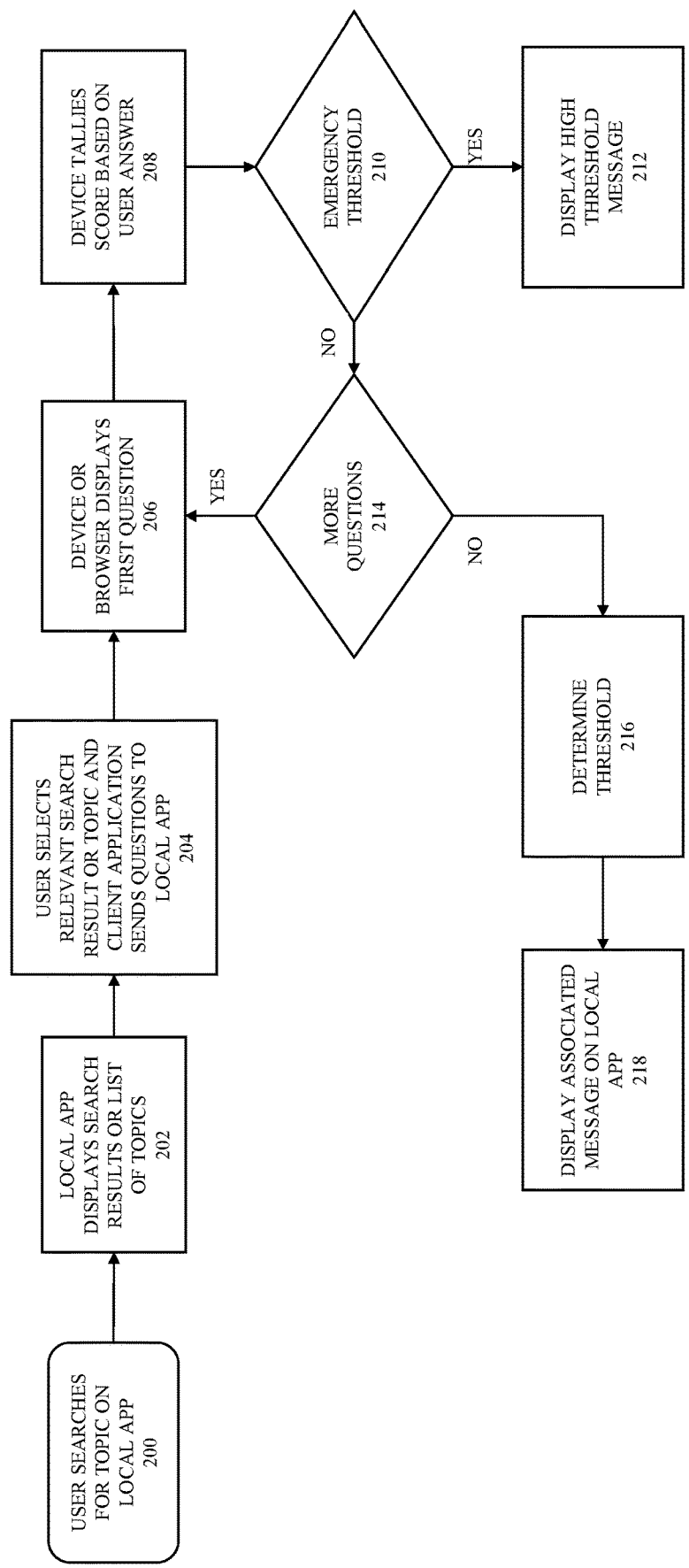
FIG. 3 shows an exemplary flowchart for answering a pet health query.

Users may access decision support features 104, such as question sets and the like, in a variety of ways. FIG. 3 shows a flow chart of an exemplary decision support process. When a user with a pet related query needs advice, the user may begin by searching at step 200 for a pet's symptoms or other health topic on the local client application. The decision support server 40 may return search results from a database in step 202 (and shown in the exemplary screenshot shown in FIG. 4A). Local client application may display a list of search results 230, along with other icons for alternative actions. Alternatively, or additionally, client application may display a list of question sets for a user to select without first performing a search at step 202. In some embodiments, question sets may be provided in a list that may be organized by topics, sub topics, or the like.

The user may then select a relevant topic at step 204. The server 40 may then send some a question set to the local client application. The local client application may store the question set and answers and may not need any additional input from the server 40 and/or database 50 where the user answers questions in the question set. In some embodiments, the client application may compare a stored version of the question set for a particular topic with that stored by server 40 and download a copy of the question set only if the server 40 has an updated version of the question set. By downloading an entire question set in this manner, the system 10 is able to utilize a thin client application that may implement the most update to date decision support functionality and question sets without needed to be recompiled and redistributed to users.

Question sets may include several pieces of information, such as header information, scoring threshold information, question information, answer information, decision information, and the like. Question sets also may include various types of questions. Preferably, the questions have predefined answers and scores and may be linked to at least one other question in the set. For example, in some embodiments, a question may have a number of mutually exclusive answers, such as a yes/no question. Yes/no questions may have two answers to a question, yes or no, and provide the same or different score for each answer. Similarly, a multiple choice question may allow a user to select one answer from a list of two or more answers and also may assign a score to each answer choice. Another question type may allow a user to select zero or more answers, such as a list of symptoms.

Figure 4B:
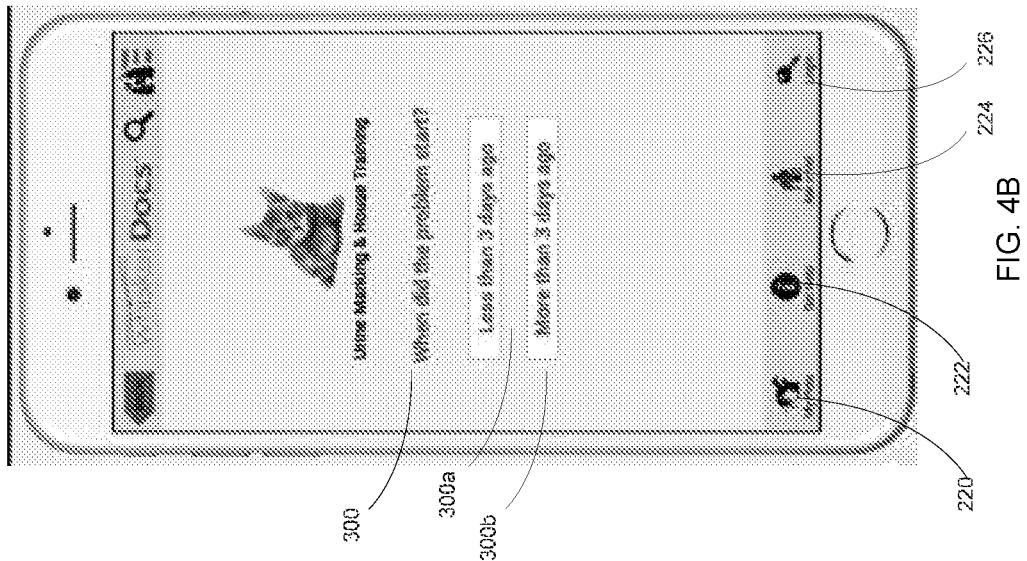
FIG. 4B shows and exemplary screenshot of a client application for an exemplary decision support system for answering a pet health query.
Figure 4A:
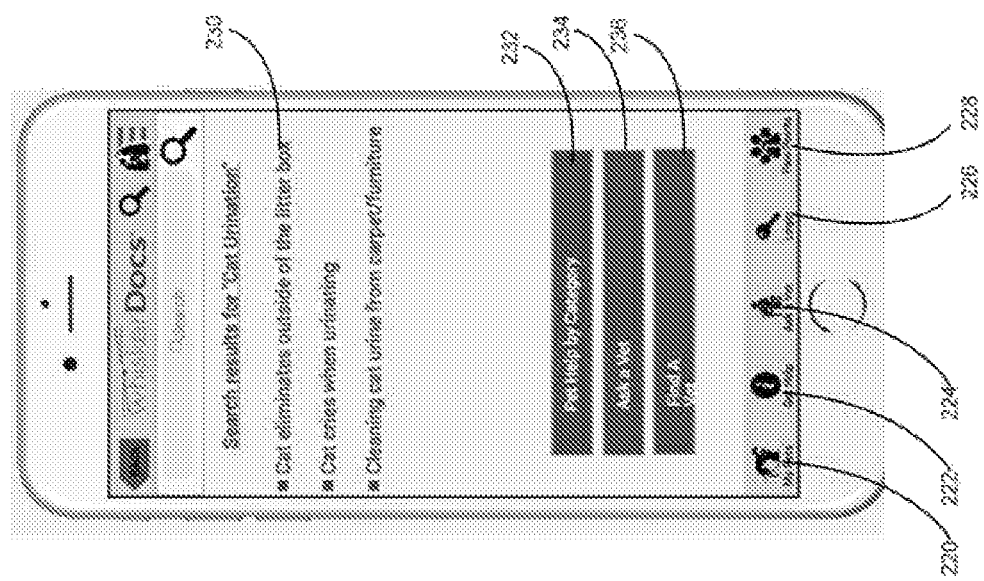
FIG. 4A shows and exemplary screenshot of a client application for an exemplary decision support system for answering a pet health query.
Figure 4D:
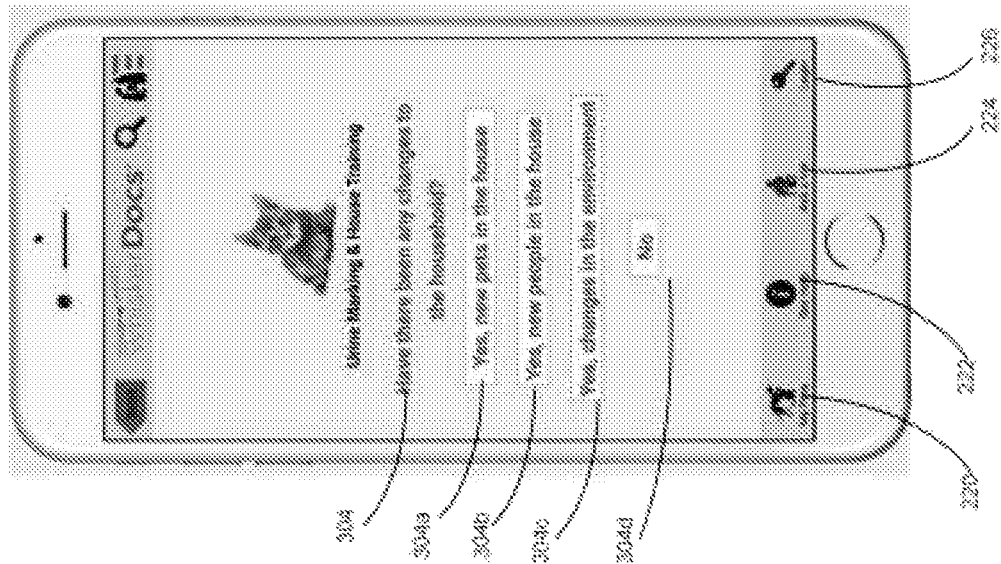
FIG. 4D shows and exemplary screenshot of a client application for an exemplary decision support system for answering a pet health query.
Figure 4C:
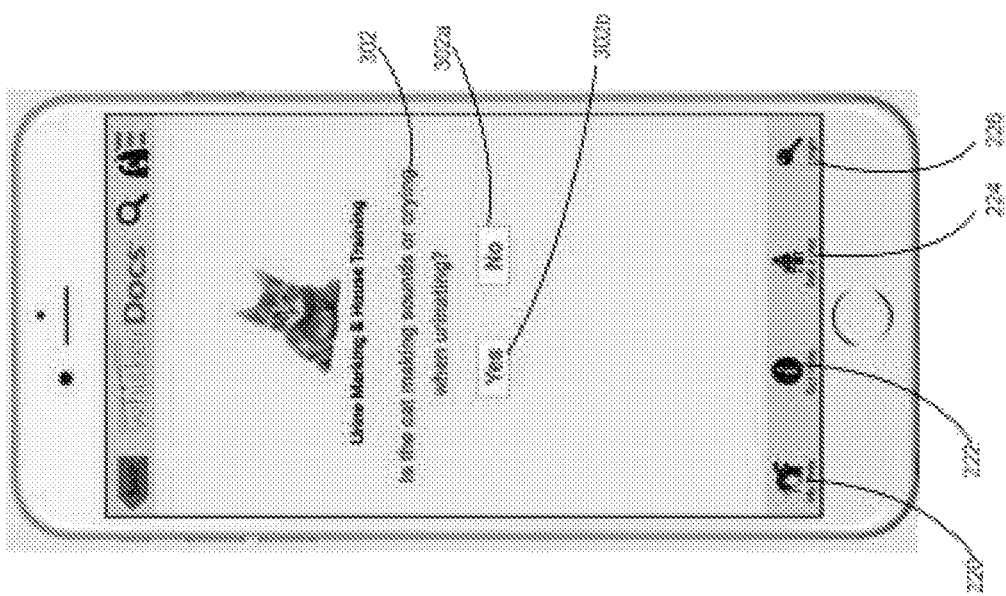
FIG. 4C shows and exemplary screenshot of a client application for an exemplary decision support system for answering a pet health query.

An exemplary yes/no question as shown in FIG. 4C. Local client application may display exemplary question 302 and answers 302a and 302b. An exemplary multiple choice question as shown in FIG. 4D. Local client application may display exemplary question 304 and answers 304a, 304b, 304c, and 304d. An exemplary zero or more question as shown in FIG. 4E. Local client application may display exemplary question 306 and answers 306a, 306b, 306c, 306d, and 306e.

Referring again to FIG. 3, the client application then may display the first question to the user at step 206, as shown in the exemplary screenshot in FIG. 4B. In some embodiments, these questions also may comprise questions that do not contribute to the score, such as background questions. These background questions may include the pet's age, sex, duration of symptoms, or the like. Exemplary question 300 and answers 300a and 300b may be used to gather background information.

Each question in a question set may have one or more associated answers. In some embodiments, each answer may be assigned a score. As users select answers, a cumulative score may be tallied and various messages may be displayed based on the score or total score. For example, scores may be multiplied, divided, or otherwise manipulated based on user inputs and for system parameters. System 10 also may allow users to enter a score for a question. In some embodiments, scores may be tallied by the client application. Alternatively or additionally, scores may be tallied by the decision support server 40.

In some embodiments, question sets also may include score values for pet demographic and health information. The pet demographic and health information may include, for example, age, gender, species, breed, heredity and pre-existing conditions, for a pet. Pet demographic and health information may be entered by the user, as noted above, or may be imported from health pet records, such as pet demographic and health information extracted from veterinarian records, other pet health applications, or any other source. For example, an age field may be included in a question set that assigns scores to specific ages or ranges of ages. As another example, a question set also may include a list of pre-existing conditions, such as diabetes, heart murmurs or the like, as well as scores for those conditions. Scores for each demographic and/or health data point may vary from question set to question set to reflect their relevance to a given health condition.

Multiple health and demographic data points may be combined and assigned a single score. For example, a male, 10-year dog with diabetes may be given a predetermined score. Alternatively, or additionally, scores for each data point may be mathematically manipulated if certain combinations of factors are present. For example, a male dog may be given a first score, a 10-year old dog may be given a second score, and a dog with diabetes may be given a third score, and these score may be added or otherwise combined to score a 10-year old male dog with diabetes. Other scoring systems also may be used.

In some embodiments, the system 10 also may incorporate answers to previous question sets. For example, answers to questions (or entire question sets) may be stored for later retrieval, such as to share with a veterinarian or the like. The system 10 may analyze previous responses to incorporate into the pet's health record. The system 10 also may provide scores for a current question set based on these previous answers, either directly from analyzing the responses or indirectly from the updated health record of the pet. In some embodiments, the relevance of previous answers may be time gated so that certain temporary conditions, such as vomiting, expire after a given time.

Referring again to FIG. 3, after the user answers a question, local client application will tally the score from the answer or answers at step 208. Local client application 10 may use other methods to calculate a score. For example, a score may be programmed into a preceding question's answer's scores, thus when the local client application reaches a final question, the answer scores will reflect the scores from all of the preceding answers without the need for the local client application to perform mathematical functions.

Figure 4F:
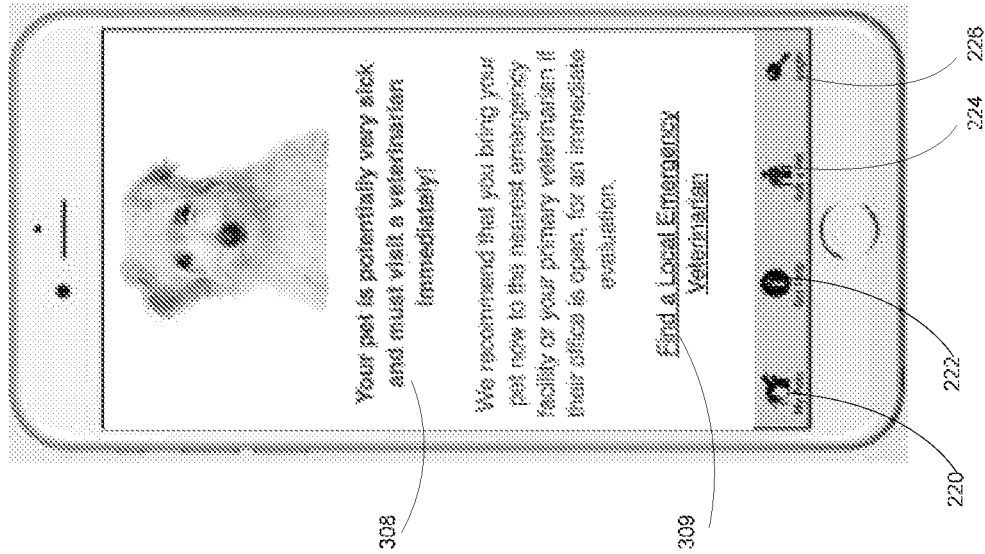
FIG. 4F shows and exemplary screenshot of a client application for an exemplary decision support system for answering a pet health query.
Figure 4E:
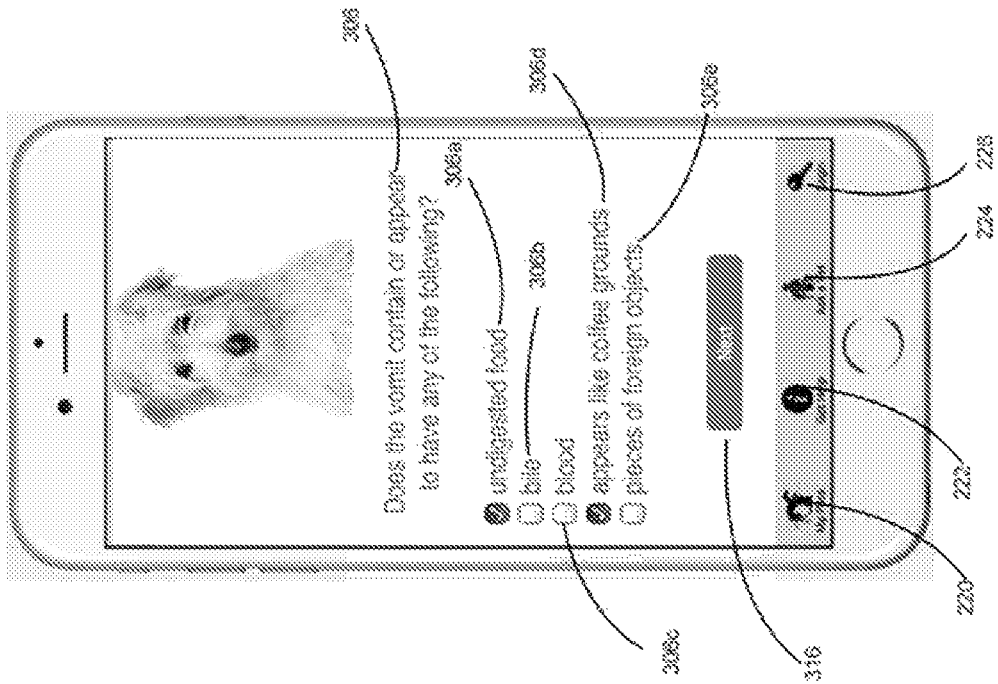
FIG. 4E shows and exemplary screenshot of a client application for an exemplary decision support system for answering a pet health query.

If the score is over a certain emergency threshold 210, local client application may display emergency threshold message 212, also shown in the exemplary screenshot in FIG. 4F. This threshold may be about 25. For example, this may tell the user to bring their pet to an emergency vet immediately, such as message 308. In addition to message 212, local client application also may display a link to allow a user to search for a local veterinarian or the like.

Returning to FIG. 3, if the score fails to reach the emergency threshold 210, the local client application may determine if there are additional questions 214 based on the questions sent previously at step 204. If there is another question, local client application may return to step 206. Once local client application loops until there are no remaining questions at step 214, the device may display a message based on the total score.

Figures 4G, 4H:
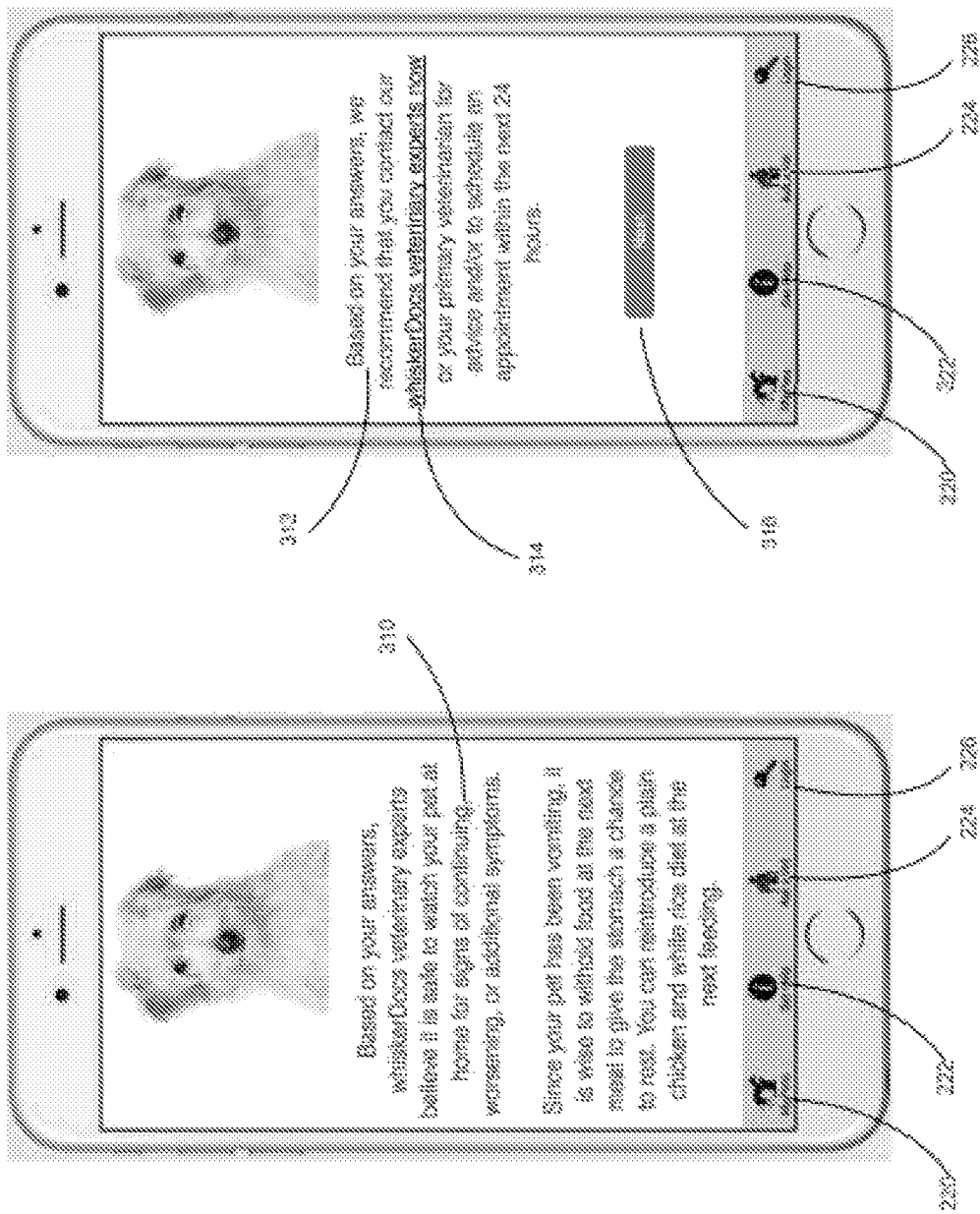
FIG. 4G shows and exemplary screenshot of a client application for an exemplary decision support system for answering a pet health query.
FIG. 4H shows and exemplary screenshot of a client application for an exemplary decision support system for answering a pet health query.

At step 216, the local client application will determine the score and determine which score threshold has been reached. Local client application then may display a message associated with the threshold at step 218. As shown in the exemplary screenshot in FIG. 4G, this message may tell the user to monitor their pet closely, as shown in message 310. As shown in the exemplary screenshot in FIG. 4H, this message may tell the user to schedule an appointment soon with the vet, as shown in message 312. In addition to displaying message 312, the local client application also may display a link to allow a user to contact a veterinarian or like using a system messaging or system chat feature.

System 10 may include additional or fewer score thresholds and corresponding messages. The preceding scores and thresholds are merely exemplary, and any score may be used to set up different alert levels based on the specific questions asked.

Figure 5:
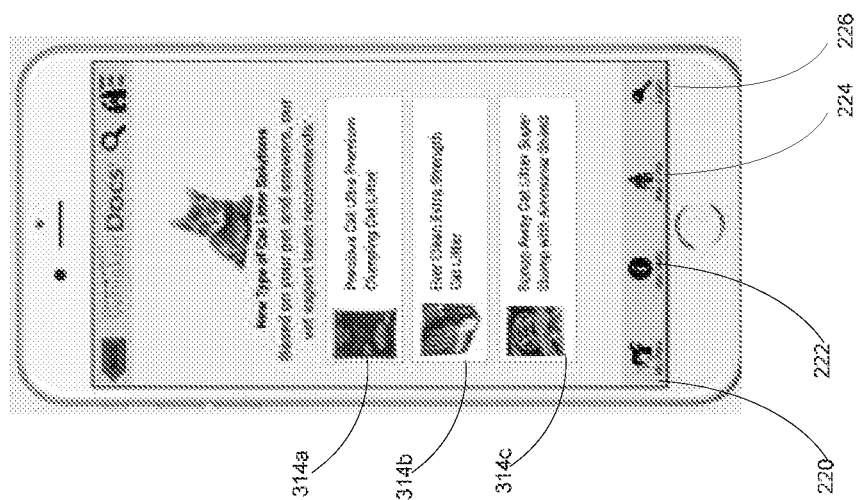
FIG. 5 shows an exemplary screenshot of a client device showing links for related products.

As shown in FIG. 5, local client application also may, after obtaining a result from the above steps, display hyperlinks 314a-c to a user that are relevant to their pet query. These hyperlinks may include links to other documentation or information about the query and/or links to products relevant to the query. An exemplary screenshot showing these links is shown in FIG. 5.

2.3 Exemplary Content Management Features

Content management system 106 may allow an administrator 110, such as a vet team, or the like, to edit the questions on database 50 through server 40. The questions may be stored on database 50 and accessed through server 40. This allows for easy updates to the questions without altering local client application. When a user opens a local client application and an internet connection is active, the application checks with server 40 if it has the most up to date copy of relevant questions and downloads the newest questions if it was out of date. If there is no network connection available at the time, the client application may use the stored question set.

3.0 Exemplary Data Elements 3.1 Exemplary Question Set Data

As noted above, question sets may include several pieces of information, such as header information, scoring threshold information, question information, answer information, decision information, and the like. More or less information also may be included in a question set. In some embodiments, question sets may be stored in an open source format, such as JavaScript Object Notation (JSON) or the like. Exemplary code which may be used to implement client applications 100 and database 50 may be found in Appendix A.

3.1.1 Exemplary Question Set Header Data

Questions set header information may include meta information for a particular question set. The following is an exemplary definition of a question set header:

{
  "ca": {
  "ext-desc": "If your dog or cat is not eating, it may be a sign of a larger problem.",
  "id": "ANOREXIA-1",
  "int-desc": "anorexia/not eating clinical algorithm for app",
  "title": "Anorexia & Not Eating",
  "use-by-system": "both"
}, In the example above, the "extdesc" field may be text used to describe the pet health topic for the set of questions to answer. The "id" field may be a unique identifier for the question set. The "intdesc" field may be a description used by content managers for the questions set. The "title" field may be a title for the topic associated with the question set.

The "usebysystem" fields may provide information about the type of client application that may access the question set.

3.1.2 Exemplary Question and Answer Information

An exemplary definition of a question may include an identifier for the question, question text, a question type and one or more answers. More or less information also may be included in the definition of a question. Each answer may be defined to include an identifier, answer text, a score associated with selection of the answer, additional information associated with the answer (such as a further explanation about the answer and the like) and a link to the next question to be asked upon selection of the answer. In some embodiments, links to the next question to be asked in the question chain may be included in the definition of the question, rather than the answer.

An exemplary definition for a yes/no question may be as follows:

```
{
  "id": "3",
  "text": "Does you cat tear apart or eat toys, yarn, or other inanimate objects?",
  "answer-type": "yes-no",
  "answers": [
    {
      "id": "1",
      "text": "Yes",
      "score": "20",
      "tip": "Cats that eat yarn or strings can develop a condition that is called a string foreign body requiring surgical intervention",
      "next-question-id": "4"
    },
    {
      "id": "2",
      "text": "No",
      "score": "0",
      "next-question-id": "4"
    }
  ],
}
```

In the above example, the "id" field may identify the question in the numbered sequence of the question set. The "text" field may provide the text of the question to be displayed. The "tip" field may define a pet health related tip that is associated with a particular question or answer. The "answer" field may define possible answers for the particular question. As noted above, each answer may include its own definition. For example, the "id" field may identify the answers in a particular question. The "text" field may include the text of the answer to be displayed. The "answertype" field may define the type of question, such as "yesno," "multiple," or "ZeroOrMore," to represent yes or no questions, multiple choice questions, or zero or more questions respectively. The "nextquestionid" field may be used to move to a new section of code when a user inputs a particular answer. The "nextquestionid" field may use a terminator to signal the end of the list of questions, such as "end." The "score" field may provide the score for the local client application 20a to tally.

An exemplary definition for a zero or more question may be as follows:

```
{
  "id": "6"
  "text": Several factors can influence snoring, select which apply.",
  "answer-type": "zeroormore",
  "answers": [
    {
      "id": "0",
      "nextquestionid": "end"
    },
    {
      "id": "1",
      "nextquestionid": "end",
      "score": "1",
      "text": "Overweight"
    },
    {
      "id": "2",
      "nextquestionid": "end",
      "score": "2",
      "text": "Nasal Problems"
    },
    {
      "id": "3",
      "nextquestionid": "end",
      "score": "3",
      "text": "High Blood Pressure"
    }
  ],
}
```

In the above example, the "id" field may identify the question in the numbered sequence of the question set. The "text" field may provide the text of the question to be displayed. The "tip" field may define a pet health related tip that is associated with a particular question or answer. The "answer" field may define possible answers for the particular question. As noted above, each answer may include its own definition. For example, the "id" field may identify the answers in a particular question. The "text" field may include the text of the answer to be displayed. The "answertype" field may define the type of question, such as "yesno," "multiple," or "ZeroOrMore," to represent yes or no questions, multiple choice questions, or zero or more questions respectively. The "nextquestionid" field may be used to move to a new section of code when a user inputs a particular answer. The "nextquestionid" field may use a terminator to signal the end of the list of questions, such as "end." The "score" field may provide the score for the local client application to tally. A zero or more question may indicate an "id" field equal to zero, which may be used by the system to indicate that a user has not selected any answer for the question. In some embodiments, a score may be associated with a response in which the user does not select any of the answer choices.

3.1.3 Exemplary Scoring Threshold Information

Exemplary code for setting thresholds may be:

```
"scoring": {
  "see-vet-threshold": "10",
  "er-threshold": "25"
},
```

The "see-vet=threshold" field may define the cumulative score required to recommend that the use see a vet, such as within a day, a week, or a month. The "er-threshold" may define the cumulative score required to identify an emergency condition and/or recommend that the user take their pet to the vet immediately. Cumulative scores falling below either threshold may trigger a different response or recommendation from the system, such as at home care, monitoring of the situation, or the like.

3.1.4 Exemplary Course of Action Information

Exemplary code for implementing the displayed result or course of action messages may be:

"results": {

"id": "end",
"text": "Based on your answers, we recommend:",
"result": [
{"id":"watchful_care", "text":"Watchful care of your pet at home. If symptoms worsen, contact your vet immediately."},
{"id":"see_vet", "text": "Calling your local vet and making an appointment as soon as possible."},
{"id":"er", "text":"This is an emergency. Take your pet to the closest emergency clinic now."}
]
}

When a preceding "nextquestionid" is "end" the program will jump to the "results" field and display the contents of the "text" field depending on the threshold reached.

3.1.5 Exemplary Data for Storing Answers for a Question Set

An exemplary data set for storing answers to a question set may be as follows:

```
{
    "ca-completed": {
        "id": "89734897",
        "pet-id": "12839082",
        "ca-id": "ANOREXIA-1",
        "total-score": 12,
        "result": "see_vet",
        "date": "01-31-2016",
        "answ-completed": [
            {
                "question-id": "1",
                "answer-id": "4"
            },
            {
                "question-id": "2",
                "answer-id": "2"
            },
            {
                "question-id": "3",
                "answer-id": "2
            }
        ]
    }
}
```

The "id" field may define a unique identifier for the completed question set. The "pet-id" field may define identifier for the pet associated with the answers. The "ca-id" field may define the question set that was answered by the user. The "total-score", "result" and "date" fields may define the cumulative score for the given answers, the recommended course of action, and the date on which the recommendation was given, respectively. The "answ-completed" field may define the identifiers of the questions and selected answers for each question in the set answered by the user.

3.1.6 Exemplary Pet and Member Data

The system may receive data from various sources in a structured format and store that data in a database, such as a relational database in the cloud. The system may be configured to access the stored data to, for example, assess the condition of a pet.

Figures 7D, 7E:
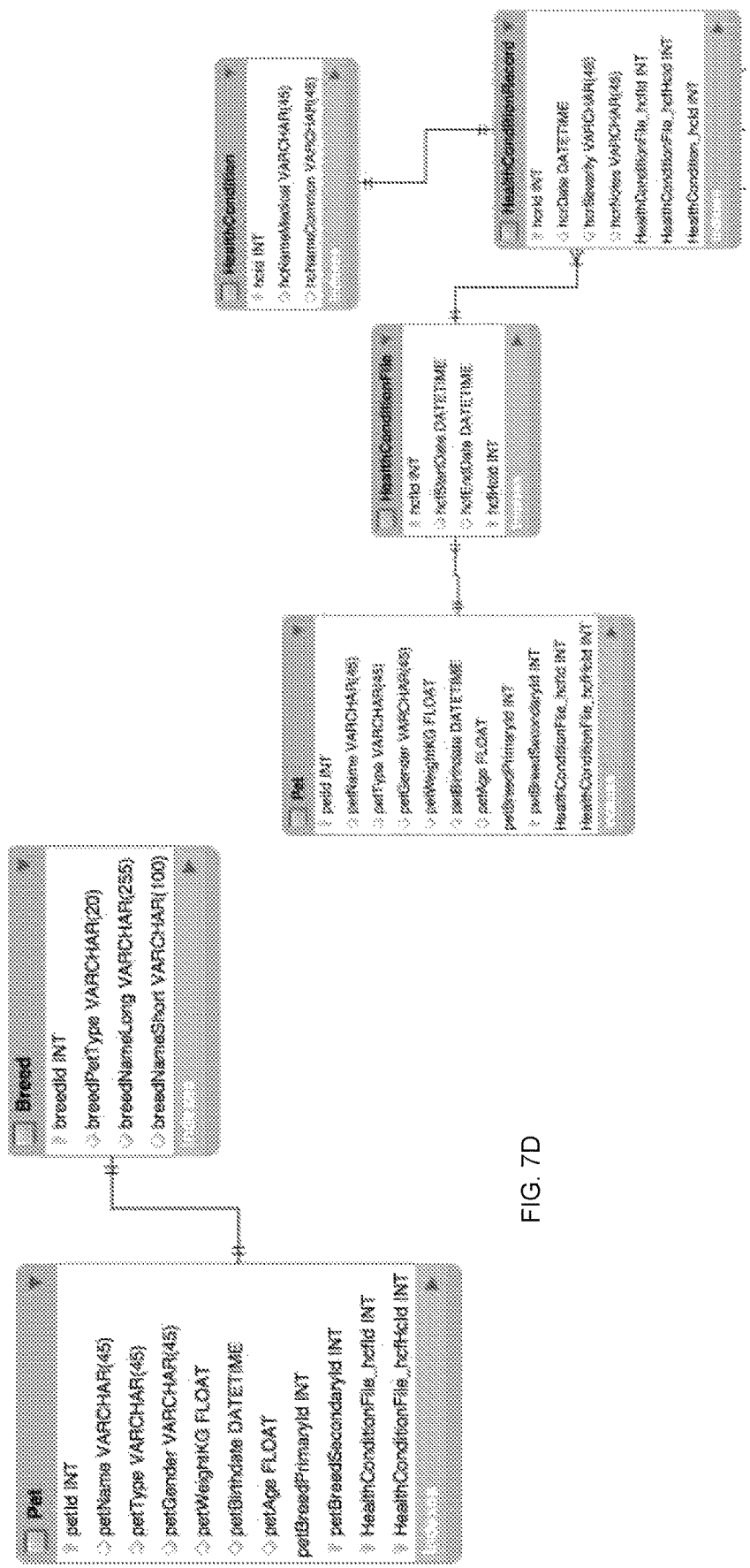
FIG. 7D illustrates and exemplary relationship of data formed by the database schema of the system.
FIG. 7E illustrates and exemplary relationship of data formed by the database schema of the system.

FIGS. 7A-7J illustrate exemplary data relationships defined by a database schema. As shown in FIGS. 7A-7C, the system may store and maintain data for the pet parent or member in a Member table. A member record may consist of fields about the member, including contact information and geographic information. Other information stored by the system may relate to, for example, billing information and insurance information.

Also, the system may store and maintain pet data in a Pet table. The Pet table may include records about a pet, such as general and/or current information about the pet. Fields within the table may include the name of the pet, the pet type, gender, weight, age/birthdate, status of spay/neuter, a primary breed, and a secondary breed. Many pets have certain probabilities of medical conditions based on the breed, and therefore determination of the breed and tracking medical information related to the breed is important to the data collection process. As shown in FIG. 7D, the pet breed is maintained in a primary and secondary field in the pet record.

The system may associate one or more pets with one or more members through a MemberToPet table. In addition, the system is configured to update certain information automatically. For instance, the age of a pet may be updated automatically based on a timing function. The system may also be configured to update certain information in response a user input. For example, the system may receive an input relating to a weight for a particular pet from a veterinary clinic and update that data in response to detecting a change in weight.

Figure 7F:
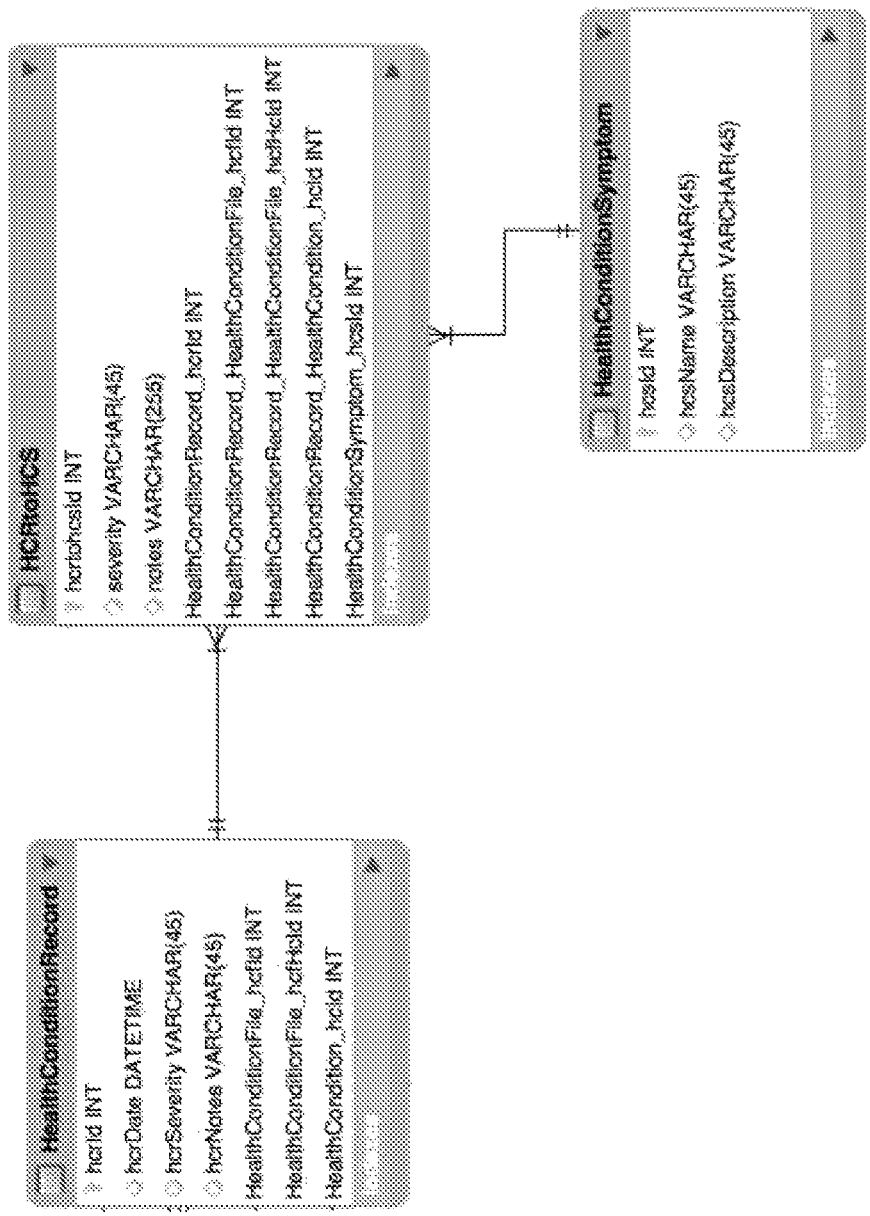
FIG. 7F illustrates and exemplary relationship of data formed by the database schema of the system.
Figures 7G, 7H:
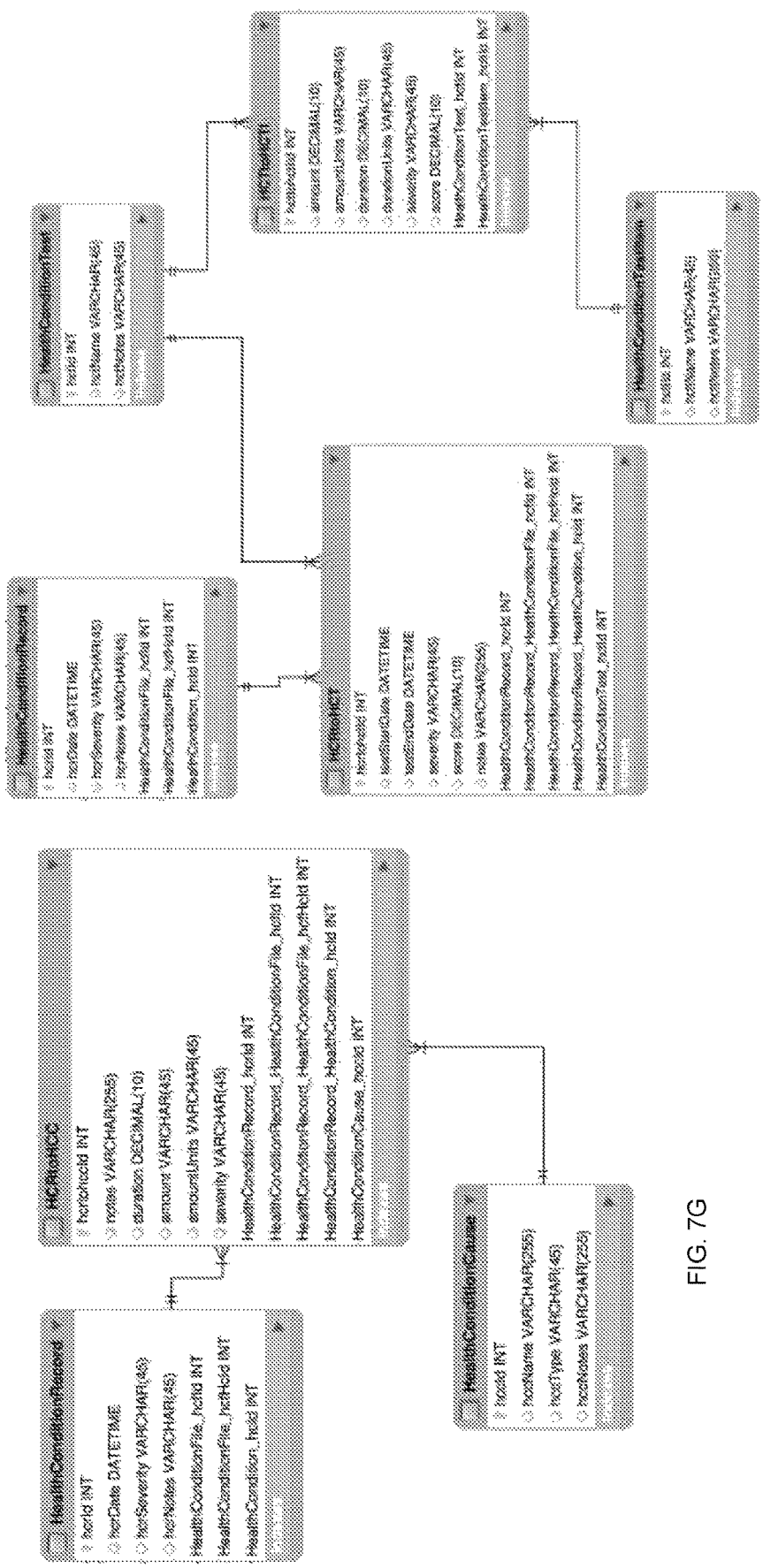
FIG. 7G illustrates and exemplary relationship of data formed by the database schema of the system.
FIG. 7H illustrates and exemplary relationship of data formed by the database schema of the system.

As shown in FIGS. 7E-7G, the system will contain a Health Condition File for each pet patient. The Health Condition File stores Health Condition Records. Each Health Condition Record is composed of one Health Condition. Health Conditions are globally defined, such that Health Condition Records reference the same body of recognized health conditions and related information. As a result, different pet records use a common library of Health Conditions, enabling consistent analysis between pet records. In certain embodiments, the system may map a pet's health conditions to a defined list in a health condition table such that a pet with a specific health condition (e.g., a specific type of cancer such as an Oral Melanoma) can be analyzed against other pet records with the same or similar health condition.

As shown in FIG. 7G, the Health Condition Record will also include Health Condition Causes. As part of a pet's individual Health Condition Cause record, a time duration and amount values are maintained, along with a severity score. The severity score may be determined as a percentage. A lower severity score means a lower probability that the cause has a large impact on the health condition.

In certain embodiments, the severity score can be manually assigned by a user, such as a veterinary professional, or automatically calculated by the system, such as through the decision support process described above. For example, an automated decision support process for ingestion of toxic substances can determine the severity of a particular toxin (i.e. chocolate ingestion in a dog) towards a specific health condition.

As shown in FIG. 7H, the Health Condition Record may also include Health Condition Tests. Health Condition Tests may relate to tests performed on a patient to help determine reasons either directly or indirectly for a condition. Tests are similar to causes, however, tests objectively measure against a known standard.

The Health Condition Record may also include Health Condition Treatments. Health Condition Treatments may relate to either direct actions to address a condition or a recommendation for next steps to address the condition. An example of a direct action may include administration of a medicine for a disease. An example of a recommendation may include consulting a specialist for a particular disease.

Figures 7I, 7J:
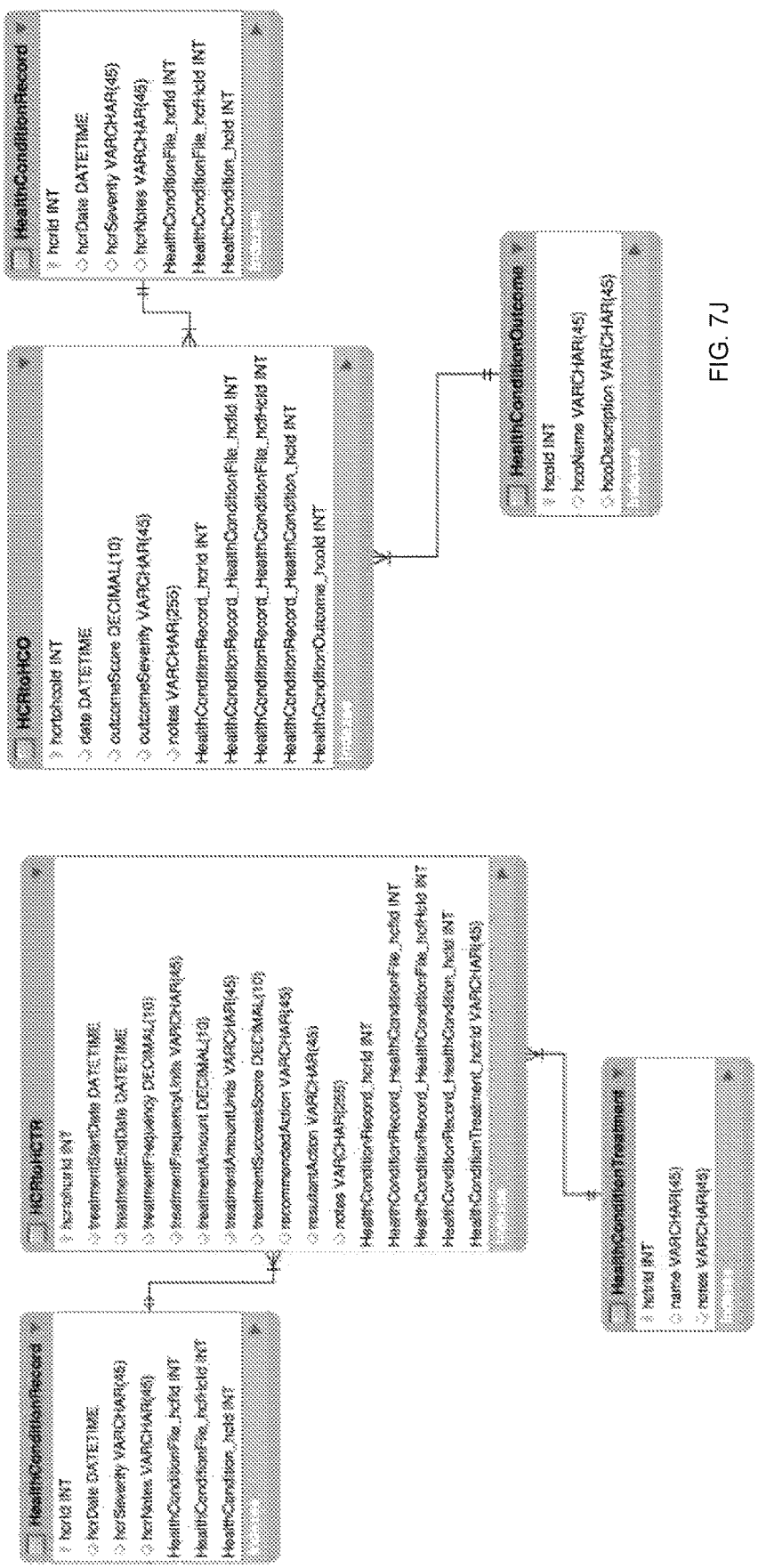
FIG. 7I illustrates and exemplary relationship of data formed by the database schema of the system.
FIG. 7J illustrates and exemplary relationship of data formed by the database schema of the system.

As shown in FIGS. 7I-7J, the Health Condition Record may also include a Health Condition Outcome. An outcome to a health condition may define the result. At the individual level, outcomes are assigned both a severity level to measure the resulting health level of the patient and a score to measure the outcome of the condition. The following table provides an exemplary severity score, severity level, and corresponding description, each of which may be displayed to a user:

| Score | 1 | 2 | 3 | 4 | 5 |
|---|---|---|---|---|---|
| Level | None or very minor | Minor | Moderate | Major | Catastrophic |
| Description | Little to no impact on the patient's life. | Minor impact to a patient's life, complications and outcome are less severe than the original health condition diagnosis | Moderate impact, complications and outcome are somewhat less severe than the original diagnosis but still substantial. | Major impact, complications and outcome are more severe than the original diagnosis. | Result in death or life-altering permanent disability. |

3.2 Exemplary Search Result or Topic List Information

An exemplary definition of search results or a topics list may be as follows:
{
"cametas": [
  {
  "code": "NOTEAT01",
  "desc": "If your dog or cat is not eating, it may be a sign of a larger problem.",
  "lastupdated": "20160827",
  "title": "Not Eating",
  "url": "https://appspot.com/_ah/api/wd/v2/ca?code=NOTEAT01"
  },
  {
  "code": "BADBRE01",
  "desc": "Bad breath can be caused by many factors, some have simple solutions, others
  are more serious.",
  "lastupdated": "20160827",
  "title": "Bad Breath",
  "url": "https://appspot.comLah/api/wd/v2/ca?code=BADBRE01"
  },
  {
  "code": "CONSTI01",
  "desc": "Constipation for your dog or cat is not only uncomfortable but can be a severe
  issue.",
  "lastupdated": "20160827",
  "title": "Constipation",
  "url": "https://appspot.comLah/api/wd/v2/ca?code=CONSTI01"
  }
  ]
}

The search results and/or topic lists may be stored in lists of API accessible lists. The "cametas" field may signal the list of pet health topics. The "code" field may signal a particular pet health topic. The "desc" field may provide a description of the pet health topic. The "lastupdated" field may provide a date that the particular topic and questions was last updated. The "title" field may provide the title of each pet health topic. The "url" field may provide the uniform resource locator address for each pet health topic question set to a local client application to allow it to download the question set.

3.3 Exemplary Data Analysis

The system is configured to analyze the data received from one or more sources to, for example, make predictions of how and when a medical condition may arise. The system may also provide treatment options to a user in response to predicting a medical condition. The system may predict a medical condition based on the analysis of an individual pet health record against global data to, for example, determine medical condition patterns that may correspond to the pet patient.

Integrated collection of pet patient data into a structured format by the system facilitates robust analysis of that data to affect both the individual patient and populations of patients based on factors including causes and symptoms of conditions and their treatment protocols.

The structured format for the integrated pet health record may include selection of a medical condition, causes, symptoms, tests, and treatments from one or more global lists. The use of global lists by the system may provide for consistency and facilitate analysis across all medical records.

Additionally, a customized version of a condition, cause, treatment, test, or outcome is generated for every Health Condition Record, enabling analysis of both the individual pet against global statistics, and individual records to be compared against one another. While a pet may have a specific medical condition that is matched to a global list, that condition is unique to that pet. For example, one pet with a recent diagnosis of diabetes may be mild compared to a pet that has had it for several years. The system may use the severity data (i.e., the score, level, and description) to produce the customized version for the record.

The system may be configured to apply machine learning algorithms to the structured data for pattern and categorization analysis. In certain preferred embodiments, the system may utilize support-vector machines, supervised artificial intelligence models with associated algorithms, for categorization.

In one instance, the system may use a supervised learning algorithm to develop a machine learning model that maps an input to an output based on a labeled data set. In particular, the system may segment a data set into training data and evaluating data. The system may use the training data to train a machine learning model and evaluate the model using the evaluating data. In certain embodiments, the evaluating data may represent benchmark clinical pet data that the system has not used for training and provides a good measure for how well the machine learning model generalizes an input. While supervised learning is one algorithm that the system may use, it is contemplated that other learning algorithms can be used to develop a machine learning model.

The system may apply labels to data, such as an assignment of a medical condition to a consistent global list. This labeling facilitates the utilization of support-vector machines to create machine learning models. Support-vector machines may create points in space, whereby points can be grouped into categories, and new examples of data can quickly be assigned to the appropriate category. In one instance, a machine learning model of a pet's weight to episodes of diabetes can be constructed from training examples. A new pet's weight can then be compared to the model for a probabilistic determination of onset of diabetes. Other machine learning techniques are also contemplated, such as Perceptron, Naïve Bayes, Decision Tree, Logistic Regression, K-Nearest Neighbor, Artificial Neural Networks, random forest, and deep learning.

Based on data from individuals applied to a global population, factors such as causes and symptoms of a condition can be categorized by the system. This analysis may involves two or more variables. In certain embodiments, the system may generate a hyperspace including N-number of variables represented by an N-dimensional space, whereby a hyperplane may categorize a population into sub-populations. As mentioned above, the system may use support-vector machine models to categorize causes and symptoms.

Once the system has categorized the data and there is a positive or negative correlation between two or more variables, that data is then made available to a pet's health record for future use. This data may allow a veterinary medical practitioner or software application to inform the pet parent of impending or occurring medical conditions based on causes or symptoms, such that better treatments and a higher occurrence of successful outcomes can be realized. In one instances, the server-side application is configured to transmit an output related to the condition of the animal to the one or more client devices, the output including a cause, a treatment, and/or an outcome.

Figure 8A:
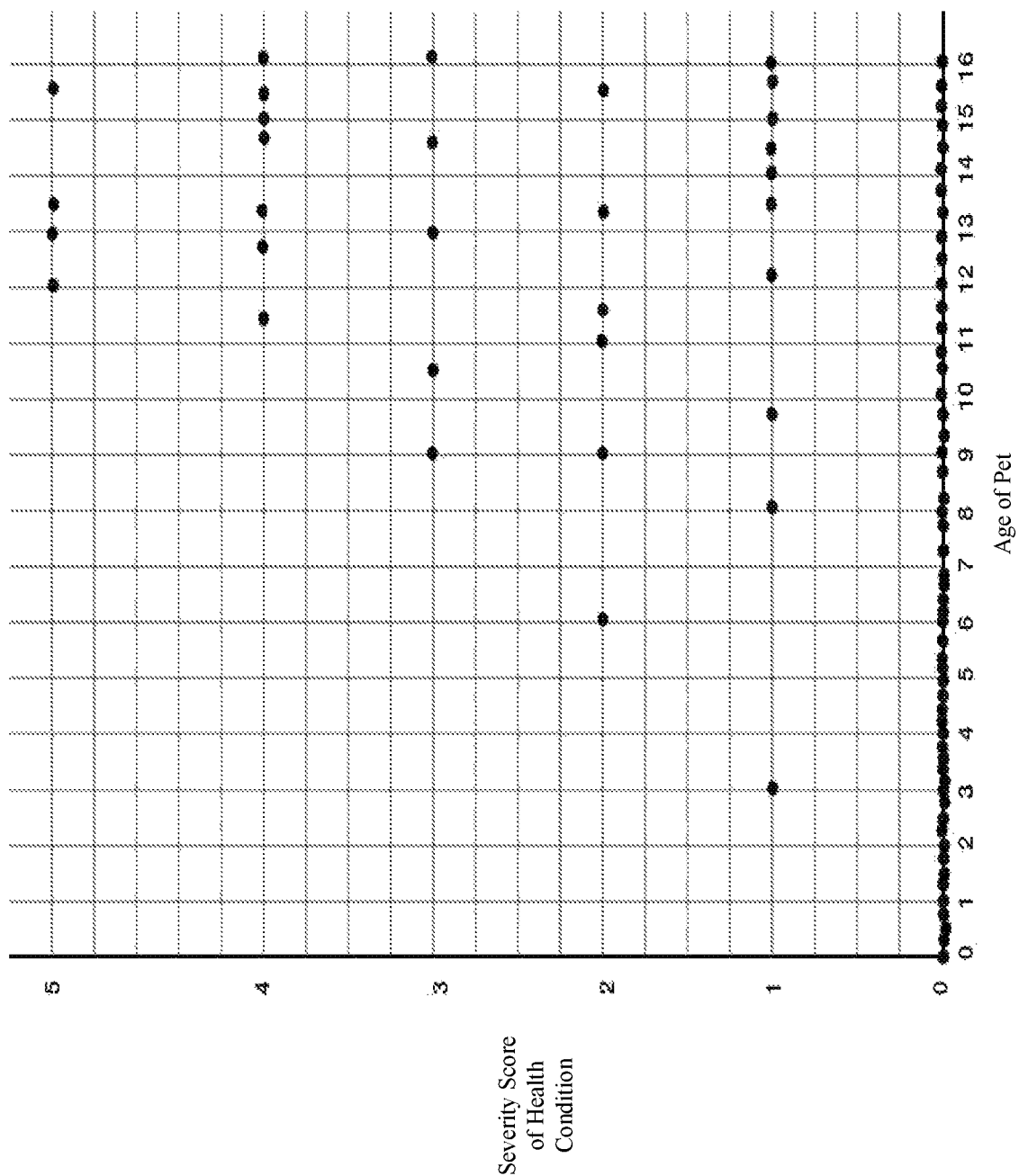
FIG. 8A illustrate an exemplary data plot generated by the system.
Figure 8B:
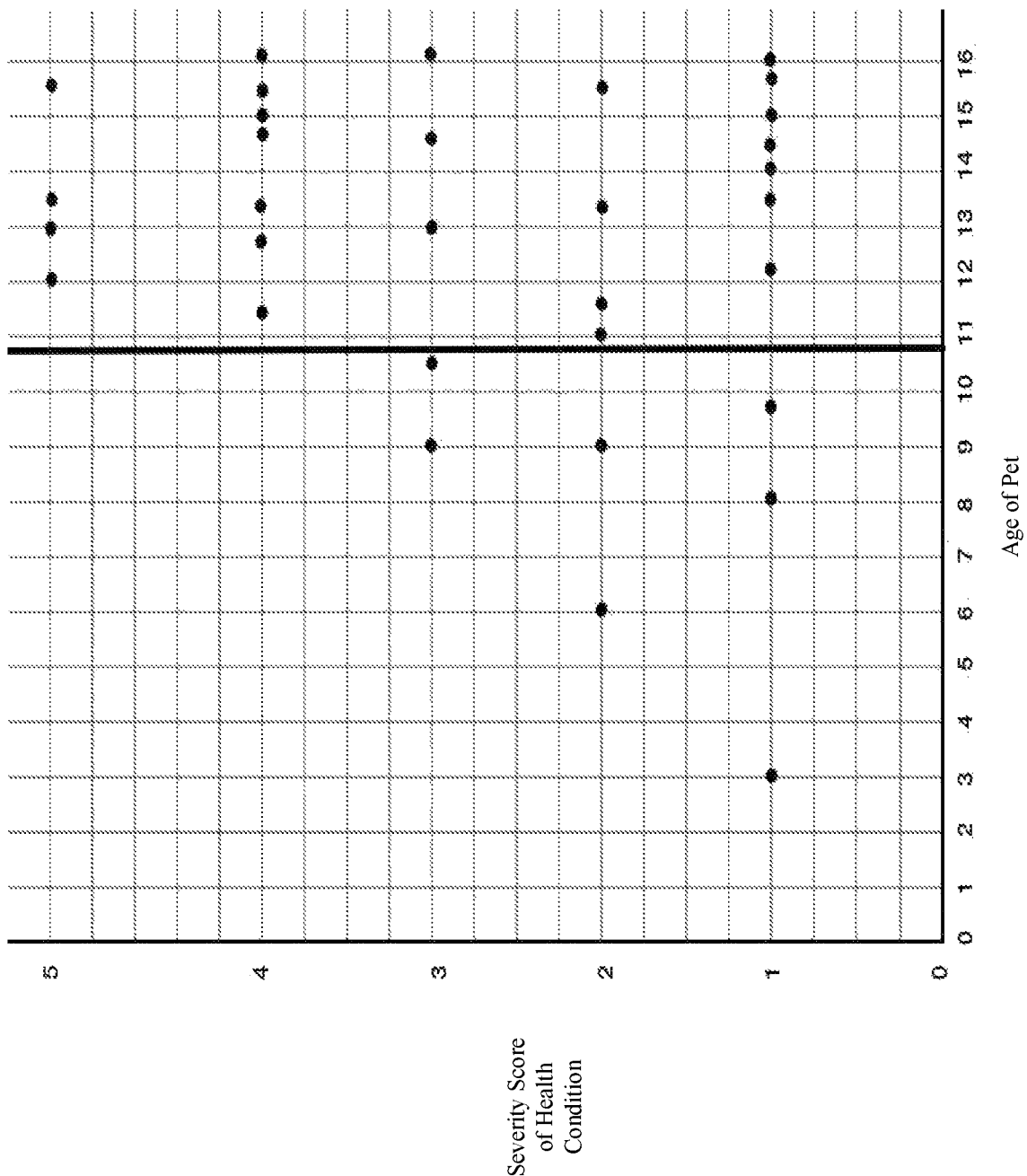
FIG. 8B illustrate an exemplary data plot generated by the system.

FIGS. 8A-8B illustrate an exemplary data plot generated by the system. In the illustrated example, the system analysis the data to identify oral melanoma (i.e., the pet's health condition) and it's incidence in relation to the age of a dog. More specifically, as shown in FIG. 8A, the severity of the oral melanoma is mapped with the dog's age to produce a plot.

Once the plot is produced, the system may utilize linear and non-linear classification to determine groupings of data. If the data is linearly separable, an optimal hyperplane is computed. Non-linear data requires the data to be mapped into a new dimensional space using a Kernel function. Kernel functions are often utilized by support-vector machines to make an optimal dimensional projection based on the data. Kernel functions include linear, polynomial, radial basis function, sigmoid, and others utilized by the system. As not all data is linear separable, the system may adjust an error-correcting parameter for differing allowances of error.

In measuring the severity of oral melanoma to the age of a pet, a hyperplane is constructed using a linear Kernel function. As shown in FIG. 8B, the system has calculated that two groupings exist, one on the left-side where the incidence of oral melanoma is low in pet ages less than 10.8 years. The right-side grouping shows pets greater than 10.8 years with a higher probable incidence of the health condition.

A new data point (test data) is evaluated against the training data utilized to find a relationship between age and the incidence of melanoma. A pet greater than 10.8 years of age is classified as higher risk to develop oral melanoma than a pet younger than 10.8 years of age. The system may further evaluate the data to, for example, define additional risk factors. For example, the system may remove all data points less than 10.8 years to determine the level of health condition risk in a pet that is 12 years old as compared to one that is 15 years old.

3.4 Exemplary Pet Health Record

An exemplary definition of pet heath record may be as follows:

```
{
    "pet": {
        "id": "12839082",
        "name": "Whiskers",
        "type": "Cat",
        "age": "4",
        "birthday": "05-22-2012",
        "gender": "Female",
        "breed": "American Shorthair",
        "spayed": "Yes",
        "weight-kg": "5",
        "med-cond": [
            {
                "id": "DIABETES-2",
                "desc": "Diabetes",
                "onset-date": "08-01-2016",
                "rem-date": "NA",
                "medication": "Basaglar"
            },
            {
                "id": "HYPOTHRY-1",
                "desc": "Hypothyroidism",
                "onset-date": "02-19-2016",
                "rem-date": "NA",
                "medication": "Felimazole"
            }
        ],
        "ca-completed": [
            {
                "id": "ANOREXIA-1",
                "result-set-id": "89734897",
                "result": "see_vet",
                "date": "01-31-2016"
            }
        ]
    }
}
```

The "idt" field may define a unique identifier for the pet. The "name" field may define the pets name. The "type" field may define the type of animal, such as cat, dog or the like. The "age" and "birthday" fields may define the pet's age (which may be calculated by the system) and birthday, respectively. The "gender" and "breed" fields may define the pet's gender and breed, respectively. The "spayed" field may define whether the pet was spayed or neutered. The "weight-kg" field may define the pet's weight in kilograms. Other units also may be used. The "med-cond" field may define zero or more past or current medical conditions of the pet, such as diabetes, hypothyroidism and the like. For each medical condition, an identifier and description of the condition may be stored along with an onset date and a remediation date, if applicable, as well as any medications that may have been prescribed and/or taken to treat the condition.

In some embodiments, records of previously completed question sets also may be stored in a pet's health record. In the above example, an identifier of the question set and the stored answers may be stored in the "id" and "result-set-id" fields, respectively. In addition, the recommended course of action and date of the recommendation also may be stored in the "result" and date fields, respectively.

4.0 Other System Functions

FIGS. 4A-4H and 5 show exemplary screenshots that local client devices 20a-c may display to a user. The screens for other local client devices and corresponding applications may be similar and/or display similar screen elements. Each screen may include navigation icons on the local client application to aid the user in using the application. These may include a My Pet icon 220, a Get Help icon 222, an Ask a Vet icon 224, a Login icon 226, a Paw Points icon 228, a Care Library icon 238, an Account icon 240 and a Next button 316. Additional or fewer icons may be used to aid user navigation. The My Pet icon 220 may allow a user to access a page containing their pet data, which may have been stored previously or may be added. The Get Help icon 222 may allow a user to access a help page to provide guidance in how to use local client application. The Ask a Vet icon 224 may allow a user to contact a veterinarian, which may be done as a live or non-live chat. The Login icon 226 may allow a user to log into their account or change their login status. The Paw Points icon 228 may allow a user to access their rewards points page. The Care Library icon 228 may allow a user to access a plurality of health articles about their pets. The Account icon 240 may allow a user to access their account screen, where she can manage and change account attributes. The Next button 316 may be used to navigate to a subsequent screen, menu, or question in the question set.

Turning now to FIG. 6, a screenshot of a customer account summary that is accessible by a registered user is shown. As shown, they system may be configured to permit a registered user access previously-created reports or pet health record entries by logging into the account, selecting the "My Account" tab from the customer portal homepage, and then selecting the report or health record entry by selecting an identifying link pertaining to that report/entry.

The health record may be accessible from any local client application having access to the internet. All of the questions the user asked a veterinarian using the system regarding a pet health issue are shown under Your Recently Submitted Questions heading 602. This may include a Status area which may display the status of the questions, i.e., whether they are solved or unsolved. The Settings heading 604 allows the user to change certain settings, such as account settings or change their password. The Notifications heading 606 displays any answers sent to the user to recently asked questions. The Service Contracts heading 608 may display current and past service contracts associated with a given user.

The "My Account" tab also may include quick access links to quickly reach a veterinarian or the like. The Ask Away link 610 may allow a user to submit a question to a veterinarian. The Chat link 612 may allow a user to chat with a veterinarian. The Ask a Vet Now link may provide a user a phone number to call a veterinarian from a telephone. The Give a Dog a Bone link 616 may allow a user to provide feedback to a system administrator or the like concerning system 10.

Further modifications and alternative embodiments of various aspects of the invention will be apparent to those skilled in the art in view of this description. Accordingly, this description is to be construed as illustrative only and is for the purpose of teaching those skilled in the art the general manner of carrying out the invention. It is to be understood that the forms of the invention shown and described in the application are to be taken as examples of embodiments. Components may be substituted for those illustrated and described in the application, parts and processes may be reversed, and certain features of the invention may be utilized independently, all as would be apparent to one skilled in the art after having the benefit of this description of the invention. Changes may be made in the elements described in the application without departing from the spirit and scope of the invention as described in the following claims.

APPENDIX A

```
{
  "ca": {
    "ext-desc": "If your dog or cat is not eating, it may be a sign of a larger problem.",
    "id": "ANOREXIA-1",
    "int-desc": "anorexia/not eating clinical algorithm for app",
    "title": "Anorexia & Not Eating",
    "use-by-system": "both"
  },
  "questions": [
    {
      "answer-type": "multiple".
      "answers": [
        {
          "id": "1",
          "next-question-id": "2",
          "score": "0",
          "text": "Cat"
        },
        {
          "id": "2",
          "next-question-id": "2",
          "score": "2",
          "text": "Kitten less than 4 months",
          "tip": "Kittens can become weak and hypoglycemic if not eating regularly"
        },
        {
          "id": "3",
          "next-question-id": "5",
          "score": "0",
          "text": "Dog"
        },
        {
          "id": "4",
          "next-question-id": "5",
```

```
          "score": "2",
          "text": "Puppy less than 6 months",
          "tip": "Kittens can become weak and hypoglycemic if not eating regularly"
        }
      ],
      "id": "1",
      "text": "Is your pet a dog or a cat?"
    },
    {
      "answer-type": "multiple",
      "answers": [
        {
          "id": "1",
          "next-question-id": "3",
          "score": "0",
          "text": "1 day or less"
        },
        {
          "id": "2",
          "next-question-id": "3",
          "score": "17",
          "text": "2-5 days",
          "tip": "Cats are unique in that their livers cannot handle large amounts of fat break down that happens when they are not eating for a long period of time causing liver damage"
        },
        {
          "id": "3",
          "next-question-id": "end",
          "score": "25",
          "text": ">5 days",
          "tip": "Cats are unique in that their livers cannot handle large amounts of fat break down that happens when they are not eating for a long period of time causing liver damage"
        }
      ],
      "id": "2",
      "text": "How long has it been since your cat has eaten?"
    },
    {
      "answer-type": "yes-no",
      "answers": [
        {
          "id": "1",
          "next-question-id": "4",
          "score": "20",
          "text": "Yes",
          "tip": "Cats that eat yarn or strings can develop a condition that is called a string foreign body requiring surgical intervention"
        },
        {
          "id": "2",
          "next-question-id": "4",
          "score": "0",
          "text": "No"
        }
      ],
      "id": "3",
      "text": "Does you cat tear apart or eat toys, yarn, or other inanimate objects?"
    },
    {
      "answer-type": "yes-no",
      "answers": [
        {
          "id": "1"
          "next-question-id": "7",
          "score": "-1".
          "text": "Yes",
          "tip": "Cats can be notoriously picky about changes in their environment; things as simple as moving a dresser or bed around in a room can sometimes cause them to stop eating"
        },
        {
          "id": "2",
          "next-question-id": "7",
          "score": "2",
          "text": "No"
        }
      ],
```

```
            "id": "4",
            "text": "Have there been any recent changes in your cats environment? (i.e. new
people or animals, rearrangement of furniture etc)"
        },
        {
            "answer-type": "multiple",
            "answers": [
                {
                    "id": "1",
                    "next-question-id": "6",
                    "score": "0",
                    "text": "1 day or less"
                },
                {
                    "id": "2",
                    "next-question-id": "6",
                    "score": "15",
                    "text": "2-5 days"
                },
                {
                    "id": "3",
                    "next-question-id": "end",
                    "score": "25",
                    "text": ">5 days"
                }
            ],
            "id": "5",
            "text": "How long has it been since your dog has eaten?",
            "tip": ""
        },
        {
            "answer-type": "yes-no".
            "answers": [
                {
                    "id": "1",
                    "next-question-id": "7",
                    "score": "20",
                    "text": "Yes",
                    "tip": "Dogs that chew up or eat toys or inanimate objects have a higher risk of
developing a blockage in the stomach or intestines"
                },
                {
                    "id": "2",
                    "next-question-id": "7",
                    "score": "0",
                    "text": "No"
                }
            ],
            "id": "6",
            "text": "Does your dog eat/tear apart toys or inanimate objects?"
        },
        {
            "answer-type": "multiple",
            "answers": [
                {
                    "id": "1",
                    "next-question-id": "8",
                    "score": "8",
                    "text": "Not at all"
                },
                {
                    "id": "2",
                    "next-question-id": "8",
                    "score": "5",
                    "text": "Will eat treats or table scraps ",
                    "tip": "You may want to try mixing in the treats or small amounts of the table
scraps into your pets regular food to try to entice eating, you may also want to try
adding broth to the regular food"
                },
                {
                    "id": "3",
                    "next-question-id": "8",
                    "score": "2",
                    "text": "Occasionally missed meals",
                    "tip": "You may want to try mixing in the treats or small amounts of the table
scraps into your pets regular food to try to entice eating, you may also want to try
adding broth to the regular food"
                }
            ],
```

```
      "id": "7".
      "text": "How much is your pet eating?",
      "tip": ""
    },
    {
      "answer-type": "yes-no"
      "answers": [
        {
          "id": "1",
          "next-question-id": "9",
          "score": "8".
          "text": "Yes"
        },
        {
          "id": "2",
          "next-question-id": "9",
          "score": "0",
          "text": "No"
        }
      ],
      "id": "8",
      "text": "Is your pet acting lethargic?",
      "tip": "
    },
    {
      "answer-type": "",
      "answers": [
        {
          "id": "1",
          "next-question-id": "end",
          "score": "25",
          "text": "Yes"
        },
        {
          "id": "2",
          "next-question-id": "10",
          "score": "0",
          "text": "No"
        }
      ],
      "id": "9",
      "text": "Is your pet's skin, eyes, or gums yellow, white, purple, or dark red?",
      "tip": ""
    },
    {
      "answer-type": "multiple",
      "answers": [
        {
          "id": "1",
          "next-question-id": "end",
          "score": "25",
          "text": "Yes >5 times an hour"
        },
        {
          "id": "2",
          "next-question-id": "11",
          "score": "10".
          "text": "Yes",
          "tip": "Drooling can also be a sign of nausea"
        },
        {
          "id": "3",
          "next-question-id": "11",
          "score": "2",
          "text": "Yes, very occasionally or history of hair balls"
        },
        {
          "id": "4",
          "next-question-id": "11",
          "score": "0",
          "text": "No"
        }
      ],
      "id": "10",
      "text": "Is your pet vomiting?",
      "tip": ""
    },
    {
      "answer-type": "yes-no",
```

```
        "answers": [
          {
            "id": "1",
            "next-question-id": "12",
            "score": "2",
            "text": "Yes >5 times an hour"
          },
          {
            "id": "2",
            "next-question-id": "12",
            "score": "0",
            "text": "No"
          }
        ],
        "id": "11",
        "text": "Is your pet having diarrhea?",
        "tip": ""
      },
      {
        "answer-type": "multiple",
        "answers": [
          {
            "id": "1",
            "next-question-id": "13",
            "score": "0",
            "text": "2 days or less"
          },
          {
            "id": "2",
            "next-question-id": "13",
            "score": "3",
            "text": "3 days or more"
          }
        ],
        "id": "12",
        "text": "How long has your pet been having diarrhea?",
        "tip": ""
      },
      {
        "answer-type": "zeroOrMore",
        "answers": [
          {
            "id": "1",
            "next-question-id": "14",
            "score": "0",
            "text": "Dry food"
          },
          {
            "id": "2",
            "next-question-id": "14",
            "score": "1",
            "text": "Canned wet food"
          },
          {
            "id": "3",
            "next-question-id": "14",
            "score": "4",
            "text": "Table scraps"
          }
        ],
        "id": "13".
        "text": "What types of food does your pet eat? (select all that apply)",
        "tip": ""
      },
      {
        "answer-type": "yes-no",
        "answers": [
          {
            "id": "1",
            "next-question-id": "end",
            "score": "25",
            "text": "Yes"
          },
          {
            "id": "2",
            "next-question-id": "14",
            "score": "0",
            "text": "No"
          }
```

```
    ],
    "id": "14",
    "text": "Is the diarrhea black or tarry or have blood in it?",
    "tip": ""
  },
  {
    "answer-type": "yes-no",
    "answers": [
      {
        "id": "1",
        "next-question-id": "15",
        "score": "-1",
        "text": "Yes"
      },
      {
        "id": "2",
        "next-question-id": "15",
        "score": "0",
        "text": "No"
      }
    ],
    "id": "15",
    "text": "Has there been a recent change in your pet's diet?",
    "tip": ""
  },
  {
    "answer-type": "yes-no"
    "answers": [
      {
        "id": "1",
        "next-question-id": "16",
        "score": "-1",
        "text": "Yes",
        "tip": "Some things that may affect the taste and palatability of pet food includes change of recipe, poor climate control during shipping, out of date, and potential contamination of the food leading to a pet refusing to eat"
      },
      {
        "id": "2",
        "next-question-id": "16",
        "score": "0",
        "text": "No"
      }
    ],
    "id": "16",
    "text": "Have you recently opened a new bag of pet food even if it is your pets normal food?",
    "tip": ""
  },
  {
    "answer-type": "yes-no".
    "answers": [
      {
        "id": "1",
        "next-question-id": "end",
        "score": "-1",
        "text": "Yes"
        "tip": "Some pets are particular about what kind of food they like and the ingredients in the food. \u00a0Sometimes things such as food sensitivity, allergy, or IBD can play a role as well"
      },
      {
        "id": "2",
        "next-question-id": "end",
        "score": "0",
        "text": "No"
      }
    ],
    "id": "17",
    "text": "Is your pet known to be a 'picky' eater?",
    "tip": ""
  }
],
"results": {
  "id": "end",
  "result": [
    {
      "id": "watchful_care",
      "text": "Watchful care of your pet at home. If symptoms worsen, contact your vet
```

```
immediately."
      },
      {
        "id": "see_vet",
        "text": "Calling your local vet and making an appointment as soon as possible."
      },
      {
        "id": "er",
        "text": "This is an emergency. Take your pet to the closest emergency clinic now."
      }
    ],
    "text": "Based on your answers, we recommend:"
  },
  "scoring": {
    "er-threshold": "25",
    "see-vet-threshold": "10"
  }
}
```

What is claimed is:

1. A system for providing non-human animal health decision support, the system comprising:
a processor; and
a non-volatile, non-transitory memory storing a module with instruction executed by the processor, the processor operative to:
collect non-human animal information including type of non-human animal;
determine a non-human animal health topic based on the collected non-human animal information;
transmit a question set corresponding to the non-human animal topic, the question set including one or more questions, each question having one or more associated answers, wherein at least one question of said question set corresponds to a medical history associated with a human owner of the animal;
receive answers associated with the question set;
analyze the answers to predict a severity of a medical condition based on the pet data and the human owner data, wherein the predicting comprises training a machine learning model based on the analyzing of the answers corresponding to the non-human animal topic and the medical history associated with the human owner, wherein said predicting further includes comparing an age of the animal to the model for a probabilistic determination of an initial onset of hypothyroidism;
determine a course of action based on the predicted severity, wherein the course of action is a recommendation comprising at least one of contacting a veterinarian, obtaining a relevant product, making an appointment with a veterinarian, watching for change in symptoms in the non-human animal, and transporting the non-human animal to a clinic; and
generate the course of action for display to a user.

2. The system of claim 1, wherein the predicted severity of the medical condition is defined as a severity score ranging from 1-5, wherein said severity score corresponds to a severity level including at least one of a minor level, a moderate level, a major level, and a catastrophic level.

3. The system of claim 2, wherein the processor is further operative to:
access the memory comprising one or more questions sets; and
obtain the question set based on the one or more symptoms associated with the non-human animal.

4. The system of claim 1, wherein the analyze step further comprises calculating a severity score based on the received answers to the question set, wherein each answer is associated with a score.

5. The system of claim 4, wherein the processor is further operative to compare the severity score to one or more predetermined thresholds, each predetermined threshold associated with one or more courses of action.

6. The system of claim 1, wherein the processor is further operative to produce at least one of a treatment option, a link to a veterinarian, a hyperlink to the relevant product, and additional information corresponding to the determined course of action.

7. The system of claim 1, wherein the processor is further operative to store the course of action and date of the recommendation.

8. A method for providing non-human animal health decision support, the method comprising:
collecting non-human animal information including type of non-human animal;
determining a non-human animal health topic based on the collected non-human animal information;
transmitting a question set corresponding to the non-human animal topic, the question set including one or more questions, each question having one or more associated answers, wherein at least one question of said question set corresponds to a medical history associated with a human owner of the animal;
receiving answers associated with the question set;
analyzing the answers to predict a severity of a medical condition based on the pet data and the human owner data, wherein the predicting comprises training a machine learning model based on the analyzing of the answers corresponding to the non-human animal topic and the medical history associated with the human owner, wherein said predicting further includes comparing an age of the animal to the model for a probabilistic determination of an initial onset of oral melanoma;
determining a course of action based on the predicted severity, wherein the course of action is a recommendation comprising at least one of contacting a veterinarian, obtaining a relevant product, making an appointment with a veterinarian, watching for change in symptoms in the non-human animal, and transporting the non-human animal to a clinic; and
generating the course of action for display to a user.

9. The method of claim 8, wherein the predicted severity is defined as a severity score ranging from 1-5, wherein said severity score corresponds to a severity level including at least one of a minor level, a moderate level, a major level, and a catastrophic level.

10. The method of claim 9, wherein the determining step further comprises:
accessing the memory comprising one or more question sets; and
obtaining the question set based on the one or more symptoms associated with the non-human animal.

11. The method of claim 8, wherein the analyzing step further comprises calculating a severity score based on the received answers to the question set, wherein each answer is associated with a score.

12. The method of claim 10, wherein the analyzing step further comprises comparing the severity score to one or more predetermined thresholds, each predetermined threshold associated with one or more courses of action.

13. The method of claim 8, wherein the generating step further comprises producing at least one of a treatment option, a link to a veterinarian, a hyperlink to the relevant product, and additional information corresponding to the course of action.

14. The method of claim 8, further comprising storing the course of action and date of the recommendation.

15. A system for providing non-human animal health decision support, comprising:
a first software module for use on a client device, the software module including instructions stored on a non-transitory computer readable medium that:
receive, via a user interface, information about a non-human animal including type of non-human animal;
determine, in response to a user input, a health topic corresponding to the non-human animal;
request, from a server computer, a question set related to the non-human animal health topic, the question set including one or more questions, each question having one or more associated answers, wherein at least one question of said question set corresponds to a medical history associated with a human owner of the animal;
present one or more questions from the question set;
detect a selection of answers corresponding to the presented one or more questions;
output a course of action via a display of the client device;
a second software module for use on a server, the second software module including instructions stored on a non-transitory computer readable medium that:
transmit, in response to the request from the client device, the question set related to the health topic;
analyze the selection of answers to predict a severity of a medical condition based on the pet data and the human owner data, wherein the predicting comprises training a machine learning model based on the analyzing of the answers corresponding to the non-human animal topic and the medical history associated with the human owner, wherein said predicting further includes comparing an age of the animal to the model for a probabilistic determination of an initial onset of oral melanoma;
determine a course of action based on the predicted severity, wherein the course of action is a recommendation comprising at least one of contacting a veterinarian, obtaining a relevant product, making an appointment with a veterinarian, watching for change in symptoms in the non-human animal, and transporting the non-human animal to a clinic;
deliver the course of action to the client device; and
store the course of action and date of the recommendation.

16. The system of claim 15, wherein the predicted severity is defined as a severity score ranging from 1-5, wherein said severity score corresponds to a severity level including at least one of a minor level, a moderate level, a major level, and a catastrophic level.

17. The system of claim 15, wherein the second module further includes instructions that:
access a database memory comprising plurality of questions sets; and
obtain the question set based on the one or more symptoms of the non-human animal.

18. The system of claim 15, wherein the second module further includes instructions that calculate a severity score based on the received answers to the question set, wherein each answer is associated with a score.

19. The system of claim 18, wherein the second module further includes instructions that compare the severity score to one or more predetermined thresholds, each predetermined threshold associated with one or more courses of action.

20. The method of claim 15, wherein outputting the course of action further includes displaying at least one of a treatment option, a link to a veterinarian, a hyperlink to the relevant product, and additional information corresponding to the course of action.

* * * * *